(12) United States Patent
Beyrath et al.

(10) Patent No.: US 11,530,190 B2
(45) Date of Patent: *Dec. 20, 2022

(54) COMPOUNDS FOR TREATING MITOCHONDRIAL DISEASE

(71) Applicant: Khondrion IP B.V., Beuningen (NL)

(72) Inventors: Julien David Beyrath, Nijmegen (NL); Mina Pellegrini, Munich (DE); Petrus Maria van Zandvoort, Beuningen (NL); Johannes Albertus Maria Smeitink, Beuningen (NL)

(73) Assignee: Khondrion IP B.V., Beuningen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/024,727

(22) Filed: Sep. 18, 2020

(65) Prior Publication Data

US 2021/0024484 A1 Jan. 28, 2021

Related U.S. Application Data

(62) Division of application No. 15/766,011, filed as application No. PCT/EP2016/074009 on Oct. 7, 2016, now Pat. No. 10,815,211.

(30) Foreign Application Priority Data

Oct. 8, 2015 (NL) .................................. 2015585

(51) Int. Cl.
  *C07D 311/66* (2006.01)
  *C07D 405/12* (2006.01)
  *C07C 235/50* (2006.01)
(52) U.S. Cl.
  CPC .......... *C07D 311/66* (2013.01); *C07C 235/50* (2013.01); *C07D 405/12* (2013.01)

(58) Field of Classification Search
  None
  See application file for complete search history.

(56) References Cited

U.S. PATENT DOCUMENTS 7,968,746 B2 * 6/2011 Jankowski ......... C07D 295/185
                                                                     564/170
2009/0118257 A1   5/2009 Jankowski et al.

FOREIGN PATENT DOCUMENTS

EP   0831092 A1   3/1998
EP   1454627 A1   9/2004
(Continued)

OTHER PUBLICATIONS

Isobe et al (2002) Synthesis and Activity of a Metabolite of (S)-6-Amino-5-(6-hydroxy-2, 5, 7, 8 tetramethylchroman-2-carboxamido)-3-methyl-1-phenyl-2, 4-(1H, 3H)-pyrimidinedione (CX-659S). Chemical and pharmaceutical bulletin, 50(10), pp. 1418-1420.

(Continued)

*Primary Examiner* — Clinton A Brooks
(74) *Attorney, Agent, or Firm* — N.V. Nederlandsch Octrooibureau

(57) ABSTRACT

The invention relates to novel compounds that are useful for modulating cellular ROS. The compounds are amide-derivatives of 2-hydroxy-2-methyl-4-(3,5,6-trimethyl-1,4-benzoquinon-2-yl)-butanoic acid. The compounds of the invention are formulated into pharmaceutical or cosmetic compositions. The invention further relates to methods wherein the compounds of the invention are used for treating or preventing diseases associated with increased ROS levels mitochondrial disorders and/or conditions associated with mitochondrial dysfunction, including adverse drug effects. The invention also relates to cosmetic methods for treating or delaying further aging of the skin and veterinary applications.

5 Claims, 15 Drawing Sheets

(56) References Cited

FOREIGN PATENT DOCUMENTS

| | | |
|---|---|---|
| EP | 2783519 A1 | 10/2014 |
| WO | WO2006/130775 A2 | 12/2006 |
| WO | WO2009/111543 A2 | 9/2009 |
| WO | WO2012/019029 A2 | 2/2012 |
| WO | WO2012/019032 A1 | 2/2012 |
| WO | WO2014/011047 A1 | 1/2014 |

OTHER PUBLICATIONS

Ji, J. et al, 2014. Antioxidant supplementation reduces genomic aberrations in human induced pluripotent stem cells. Stem Cell Reports, 2(1), pp. 44-51.

West, A.P. et al, 2011. Mitochondria in innate immune responses. Nature Reviews Immunology, 11(6), p. 389.

Benit P. et al, 2010. Genetic background influences mitochondrial function: modeling mitochondrial disease for therapeutic development. Trends in molecular medicine, 16(5), pp. 210-217.

Klopstock T. et al, 2011. A randomized placebo-controlled trial of idebenone in Leber's hereditary optic neuropathy. Brain, 134(9), pp. 2677-2686.

Angelin A. et al, 2007. Mitochondrial dysfunction in the pathogenesis of Ullrich congenital muscular dystrophy and prospective therapy with cyclosporins. Proceedings of the National Academy of Sciences, 104(3), pp. 991-996.

Merlini et al, 2008. Cyclosporin A corrects mitochondrial dysfunction and muscle apoptosis in patients with collagen VI myopathies. Proceedings of the National Academy of Sciences, 105(13), pp. 5225-5229.

Distelmaier F. et al, 2012. Trolox-sensitive reactive oxygen species regulate mitochondrial morphology, oxidative phosphorylation and cytosolic calcium handling in healthy cells. Antioxidants & redox signaling, 17(12), pp. 1657-1669.

* cited by examiner

COMPOUNDS FOR TREATING MITOCHONDRIAL DISEASE

FIELD OF THE INVENTION

The invention relates to the field of human and animal diseases and cosmetics. The invention in particular relates to amide-derivative of 2-hydroxy-2-methyl-4-(3,5,6-trimethyl-1,4-benzoquinon-2-yl)-butanoic acid for treating conditions that are associated with oxidative stress, mitochondrial dysfunction or mitochondrial deficiencies, including adverse drug effects causing oxidative stress or mitochondrial dysfunction, and for cosmetic use against aging of the skin.

BACKGROUND OF THE INVENTION

Reactive oxygen species (ROS) are involved in a broad spectrum of cellular processes, such as cell signalling, apoptosis and homeostasis. This implicates a crucial role for ROS in normal cellular function. However, (too) high levels of ROS may cause significant damage to cell structures, which is known as oxidative stress. Oxidative stress is thought to be involved in the development of many different diseases, such as Asperger syndrome, ADHD, cancer, Parkinson's disease, Lafora disease, Alzheimer's disease, atherosclerosis, heart failure, myocardial infarction, fragile X syndrome, Sickle Cell Disease, lichen planus, vitiligo, autism, infection, congenital muscular dystrophies, dystrophinopathies and chronic fatigue syndrome. Furthermore, it has recently been shown that supporting the cellular redox homeostasis is also important in many ex vivo techniques, such as during the induction of pluripotent stem cells (Ji et al, Stem cell reports (2014) vol. 2: 44-51).

A major source of reactive oxygen species is mitochondria. Mitochondria are essential organelles that constitute the 'powerhouses' of the cell. Defects in these organelles often lead to a variety of severe metabolic disorders affecting the organs that have a high-energy demand, such as muscle and brain. With an incidence of at least 1 in 5000 individuals it is recognized as the most common group of inborn errors of metabolism. Moreover, because programmed cell death (apoptosis) is triggered by mitochondria, defects in these organelles have consequences far beyond the diseases, which brought them initially to our attention and involvement in cancer and neurodegenerative diseases like Alzheimer and Parkinson has been demonstrated. Many commonly used drugs like the NRTIs, certain antibiotics and anti-epileptic drugs, may cause mitochondrial dysfunction. So far no effective treatment is available to cure or improve these disease conditions.

One of the primary functions of mitochondria is oxidative phosphorylation (OXPHOS). The molecule adenosine triphosphate (ATP) functions as an energy "currency" or energy carrier in the cell, and eukaryotic cells derive the majority of their ATP from biochemical processes carried out by mitochondria, including the citric acid cycle, which generates reduced $NADH+H^+$ from oxidized $NAD^+$, and OXPHOS, during which $NADH+H^+$ is oxidized back to $NAD^+$. The electrons released by oxidation of $NADH+H^+$ are shuttled down a series of protein complexes (Complex I, Complex II, Complex III, and Complex IV) known as the mitochondrial respiratory chain. These complexes are embedded in the inner membrane of the mitochondrion. Complex IV, at the end of the chain, transfers the electrons to oxygen, which is reduced to water. The energy released as these electrons traverse the complexes is used to generate a proton gradient across the inner membrane of the mitochondrion, which creates an electrochemical potential across the inner membrane. Another protein complex, Complex V (which is not directly associated with Complexes I, II, III and IV) uses the energy stored in the electrochemical gradient to convert ADP into ATP.

Mitochondrial oxidative phosphorylation is a major cellular source of reactive oxygen species (ROS), as approximately 1-2% of oxygen consumed during physiological respiration is converted into superoxide ($.O_2^-$) when electrons prematurely leak from the electron transport chain and are aberrantly transferred to molecular oxygen. However, under specific metabolic or stress conditions, more electrons can prematurely exit the respiratory chain to further augment mitochondrial superoxide generation. Leakage occurs at complex I, complex II or complex III, although complex I and complex III are the major sites of superoxide generation within mitochondria (Philip West A, Nature Reviews Immunology 2011 (11):389-402).

The contribution of mitochondrial dysfunction to human disease was already recognised in the late 1980s, when maternally inherited point mutations, as well as deletions arising spontaneously during development, were found to be associated with rare neurological syndromes. Mitochondrial dysfunction contributes to various disease states. Some mitochondrial diseases are due to mutations or deletions in the mitochondrial genome. If a threshold proportion of mitochondria in the cell is defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved. Some examples of mitochondrial diseases are Friedreich's ataxia (FRDA), Leber's Hereditary Optic Neuropathy (LHON), dominant optic atrophy (DOA); mitochondrial myopathy, encephalopathy, lactacidosis, and stroke (MELAS), Myoclonus Epilepsy Associated with Ragged-Red Fibers (MERRF) syndrome, Leigh syndrome, and oxidative phosphorylation disorders. Mitochondrial diseases involve children and adults who manifest the signs and symptoms of accelerated aging, including neurodegenerative diseases, stroke, blindness, hearing impairment, diabetes, and heart, liver and kidney failure and myopathies.

Very few treatments are available for patients suffering from these mitochondrial diseases. The drug idebenone (a $CoQ_{10}$ variant) has been approved for the treatment of Friedreich's ataxia (Benit et al., 2010, Trends Mol Med, 16:210-7; Klopstock et al., 2011, Brain, 134:2677-86) and LHON. Another compound, $MitoQ_{10}$ (mitoquinone), has been proposed for treating mitochondrial disorders (U.S. Pat. No. 7,179,928) but clinical results for MitoQ have not yet been reported. A successful treatment strategy has been developed for patients with a secondary mitochondrial disorder involving Ullrich's congenital muscular dystrophy and Bethlem's myopathy. The pathogenic mechanism in these myopathies involves inappropriate opening of the mitochondrial permeability transition pore. This action was prevented in patients treated with the permeability-transition-pore desensitizer CSA (cyclosporin A; Angelin et al., 2007, Proc Natl Acad Sci USA, 104:991-6; Merlini et al., 2008, Proc Natl Acad Sci USA, 105:5225-9).

An overview of current clinical trials relating to mitochondrial disease can be found online (www.clinicaltrials.gov/ct2/results?term=mitochondrial+disease); this include studies of CoQ10 for the treatment of muscle weakness and mitochondrial diseases, dietary supplements for MELAS, EPI-743 for mitochondrial diseases, human growth hormone for obesity, nutritional therapy for diabetes, pioglitazone for diabetes, idebenone for MELAS, and vitamin E for mitochondrial trifunctional protein deficiency.

WO 2012/019032 discloses methods of treatment, prevention, or suppression of symptoms associated with a mitochondrial disorder and/or modulating, normalizing, or enhancing one or more energy biomarkers, whereby vitamin K analogues are administered.

WO 2012/019029 discloses methods of treatment, prevention, or suppression of symptoms associated with a mitochondrial disorder and/or modulating, normalizing, or enhancing one or more energy biomarkers, whereby naphtoquinones and derivatives thereof are administered.

Distelmaier et al. (2012, Antioxid Redox Signal. 17 (12):1657-69) disclose that Trolox™ (6-hydroxy-2,5,7,8-tetramethylchroman-2-carboxylic acid) reduces the levels of ROS, increased mitofusins-mediated mitochondrial filamentation and expression of mitochondrial complex I, activity of citrate synthase and OXPHOS enzymes and cellular 02 consumption in cultured healthy human skin fibroblasts.

WO 2014/011047 discloses methods for treating or preventing mitochondrial disorders, conditions associated with mitochondrial dysfunction and/or neoplastic diseases, using Trolox-derivatives. In particular, these derivatives can be used in modulating mitochondrial morphology and/or expression of OXPHOS enzymes and/or cellular ROS. WO 2014/011047 discloses Trolox derivatives, wherein the carboxylic acid moiety is replaced by an amide moiety and wherein the nitrogen atom of the amide moiety is connected via a linker to a cationic nitrogen atom.

Besides the role of ROS in a wide variety of diseases and conditions, excessive ROS levels also play an important role during the transformation of somatic cells into induced pluripotent stem cells. In particular, increased levels of ROS and oxidative stress damage has been observed during the early stages of reprogramming somatic cells into pluripotent stem cells. Notably, the addition of antioxidants appeared to reduce both ROS and double stranded breaks, resulting in lower apoptotic rates (Ji et al, supra). There is however still a need in the art for effective means to modulate ROS levels. Furthermore, there is still a need for effective means for modulating mitochondrial function for them to be used in treatments of mitochondrial disease and/or conditions associated with mitochondrial dysfunction or for cosmetic use.

SUMMARY OF THE INVENTION

In a first aspect the invention pertains to novel amide-derivatives of 2-hydroxy-2-methyl-4-(3,5,6-trimethyl-1,4-benzoquinon-2-yl)-butanoic acid, which are represented by general structure (I):

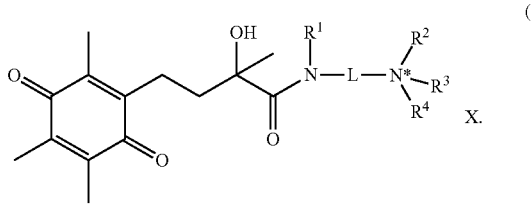

Herein,

L is a linker between the amide nitrogen atom and the distal nitrogen atom (N*) comprising 1 to 10 optionally substituted backbone atoms selected from carbon, nitrogen and oxygen;

$R^1$ and $R^2$ are each independently selected from hydrogen (H), $C_1$-$C_6$ alkyl or $C_1$-$C_6$ alkenyl, or $R^1$ and $R^2$ are joined together and thus form a second linker between the amide nitrogen atom and the distal nitrogen atom, or $R^1$ is joined with a backbone atom of the linker L in a cyclic structure and/or $R^2$ is joined with a backbone atom of the linker L in a cyclic structure;

$R^3$ is selected from hydrogen (H), $C_1$-$C_6$ alkyl or $C_1$-$C_6$ alkenyl, wherein the alkyl or alkenyl moiety may be substituted with one or more halogen atoms or (halo) alkoxy moieties, or $R^3$ is absent when the distal nitrogen atom is part of an imine moiety; and in case the distal nitrogen atom is in cationic form (i.e. the compound is in salt form): $R^4$ is selected from hydrogen (H) or $C_1$-$C_6$ alkyl, wherein the alkyl moiety may be substituted with one or more halogen atoms or (halo)alkoxy moieties and X is an anion, preferably a pharmaceutically acceptable anion; or in case the distal nitrogen atom is in neutral form: $R^4$ and X are absent.

Preferred compounds according to the first aspect of the invention are those wherein $R^4$=H and X=Cl$^-$ or wherein $R^4$ and X are absent and wherein:

L=L, $R^1$-$R^2$=$L^1$, $R^3$=H;
L=$L^1$, $R^1$=H, $R^2$=H, $R^3$=H;
L=$L^2$, $R^1$=H, $R^2$=H, $R^3$=H;
L=$L^3$, $R^1$=H, $R^2$=H, $R^3$=H;
L=$L^4$, $R^1$=H, $R^2$=H, $R^3$=absent;
L=$L^5$, $R^1$=H, $R^2$=H, $R^3$=absent;
L=$L^6$, $R^1$=H, $R^2$=H, $R^3$=absent;
L=$L^3$, $R^1$=H, $R^2$=Me, $R^3$=Me;
L=$L^1$, $R^1$=H, $R^2$=Me, $R^3$=Me;
L=$L^7$, $R^1$=H, $R^2$=H, $R^3$=absent;
L=$L^1$, $R^1$=H, $R^2$=H, $R^3$=absent;
L=$L^9$, $R^1$=H, $R^2$=H, $R^3$=absent;
L=$L^{10}$, $R^1$-$R^{1'}$=$L^1$, $R^2$=H, $R^3$=absent;
L=$L^{11}$, $R^1$=H, $R^2$=H, $R^3$=H;
L=$L^{12}$, $R^1$=H, $R^2$=H, $R^3$=absent;
L=$L^{13}$, $R^1$=H, $R^2$=H, $R^3$=H;
L=$L^{14}$, $R^1$=H, $R^2$=H, $R^3$=H;
L=$L^{15}$, $R^1$=H, $R^2$=H, $R^3$=H;
L=$L^{15}$, $R^1$=H, $R^2$=Me, $R^3$=Me
L=$L^{16}$, $R^1$=H, $R^2$=H, $R^3$=H;
L=$L^{17}$, $R^1$=H, $R^2$=H, $R^3$=H;
L=$L^{16}$, $R^1$=H, $R^2$=Me, $R^3$=Me;
L=$L^{18}$, $R^1$=H, $R^2$-$R^{2'}$=$L^3$, $R^3$=H;
L=$L^{19}$, $R^1$=H, $R^2$-$R^{2'}$=L, $R^3$=H;
L=$L^{20}$, $R^1$=H, $R^2$=H, $R^5$-$R^{5'}$=$L^3$, $R^3$=absent;
L=$L^{21}$, $R^1$=H, $R^2$-$R^{2'}$=$L^1$, $R^3$=H;
L=$L^{22}$, $R^1$-$R^{1'}$=$L^1$, $R^2$=TH, $R^3$=H;
L=$L^{23}$, $R^1$-$R^{1'}$=$L^1$, $R^2$=TH, $R^3$=H;
L=$L^{24}$, $R^1$-$R^{1'}$=$L^3$, $R^2$=H, $R^3$=H;
L=$L^{25}$, $R^1$-$R^{1'}$=$L^3$, $R^2$=H, $R^3$=absent;
L=$L^{26}$, $R^1$=H, $R^2$=H, $R^5$-$R^{5'}$=$L^1$, $R^3$=H.
L=$L^{19}$, $R^1$=H, $R^2$-$R^{2'}$=$L^3$, $R^3$=Me;
L=$L^{19}$, $R^1$=H, $R^2$-$R^{2'}$=$L^1$, $R^3$=H; or
L=$L^{21}$, $R^1$=H, $R^2$-$R^{2'}$=$L^1$, $R^3$=Me.

In a second aspect, the invention relates to a compound according to the invention for use as a medicament.

In a further aspect, the invention pertains to method of treating, preventing, or suppressing symptoms associated with a pathology, condition or disorder associated with an increased or a decreased ROS level, the method comprising administering to a subject an effective amount of one or more compounds according to the invention as defined herein above. Alternatively, the invention relates to a compound according to the invention for use in treating, preventing or suppressing symptoms associated with a pathology, condition or disorder associated with an increased or a decreased ROS level. Preferably, the compound according to the invention can be used in treating, preventing or suppressing symptoms associated with a pathology, condition or disorder associated with an increased ROS level.

In a further aspect, the invention relates to a method of treating, preventing, or suppressing symptoms associated with a mitochondrial disorder or with a condition associated with mitochondrial dysfunction, the method comprising administering to a subject an effective amount of one or more compounds according to the invention as herein defined above. Alternatively, the invention relates to a compound according to the invention for use in a method of treating, preventing, or suppressing symptoms associated with a mitochondrial disorder or with a condition associated with mitochondrial dysfunction.

Further aspects of the invention relate to the cosmetic use of the compounds according to the invention, wherein the compounds may be used (in methods) to revive the skin of a treated individual, particularly in individuals with aged skin, either due to aging or due to excessive exposure to sun, to compounds according to the invention for use as a conservative agent, for use in research applications, such as in vitro, in vivo, or ex vivo experiments in order to modulate one or more energy biomarkers in an experimental system, for use in biochemical tests or assays.

In yet further aspects, the invention pertains to pharmaceutical or cosmetic composition comprising a compound according to the invention, and to articles of manufacture and kits comprising a compound according to the invention. A particular aspect of the invention concerns a cosmetic method for treating or delaying further aging of the skin in a subject, the method comprising the step of administering to the skin of the subject an effective amount of a composition comprising a compound as defined herein. The compounds according to the invention are surprisingly effective in reducing ROS levels, as evidenced in the examples, and are thus particularly suitable in such a method.

In another aspect, the invention relates to an ex vivo method for scavenging reactive oxygen species in a cell, wherein the method comprises a step of exposing the cell to a compound of the invention. The compounds according to the invention are surprisingly effective in reducing ROS levels, as evidenced in the examples, and are thus particularly suitable in such a method. Preferably, the cell is a somatic cell, a gamete, a gametocyte or an undifferentiated stem cell. More preferably, the somatic cell is further reprogrammed to an induced pluripotent stem cell (iPSC) by exposing the cell to at least one reprogramming factor. The reprogramming factor is preferably at least one of Oct4, Sox2, KLF4, c-Myc, Lin28, Nanog, Glis1, Sall4, Esrrb and Nr5a2 and the somatic cell is preferably a fibroblast, neuronal (progenitor) cell, hepatocyte, B cell, kidney cell, muscle cell, adrenal gland cell, keratinocyte, melanocyte, epithelial cell or a peripheral blood derived cell, preferably wherein the peripheral blood derived cell is an endothelial progenitor cell (L-EPCs) or a cord blood derived cell type (CD34+).

DESCRIPTION OF THE INVENTION

In a first aspect the invention pertains to a compound which is an amide-derivative of 2-hydroxy-2-methyl-4-(3,5,6-trimethyl-1,4-benzoquinon-2-yl)-butanoic acid (compound A). Compound A is the ring-opened form of 6-hydroxy-2,5,7,8-tetramethylchroman-2-carboxylic acid (Compound B), which is also known under trademark name Trolox. Compound A is also referred to as "open-Trolox".

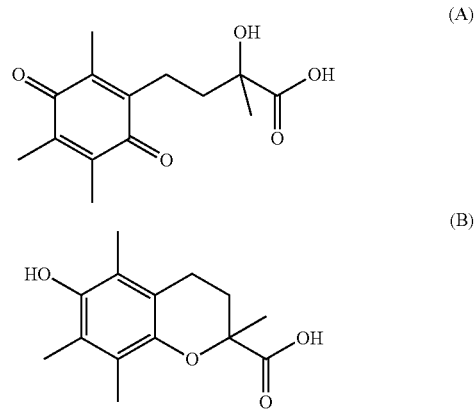

In a compound of the invention, the carboxylic acid moiety of compound A is replaced by an amide moiety, wherein the nitrogen atom of the amide moiety is connected via a linker to a distal nitrogen atom. In the context of the present invention, the nitrogen atom that is closest to the open-Trolox core of compound A is referred to as the "amide nitrogen atom" and the nitrogen atom that is farthest away from the open-Trolox core is referred to as the "distal nitrogen atom". Additional nitrogen atoms may be present in the linker. The distal nitrogen atom may be in neutral form or in cationic form.

The compound of the invention may be identified by general structure (I):

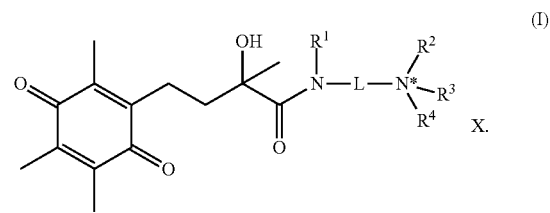

Herein,

L is a linker between the amide nitrogen atom and the distal nitrogen atom (N*) comprising 1 to 10 optionally substituted backbone atoms selected from carbon, nitrogen and oxygen;

$R^1$ and $R^2$ are each independently selected from hydrogen (H), $C_1$-$C_6$ alkyl or $C_1$-$C_6$ alkenyl, or $R^1$ and $R^2$ are joined together and thus form a second linker between the amide nitrogen atom and the distal nitrogen atom, or $R^1$ is joined with a backbone atom of the linker L in a cyclic structure and/or $R^2$ is joined with a backbone atom of the linker L in a cyclic structure;

$R^3$ is selected from hydrogen (H), $C_1$-$C_6$ alkyl or $C_1$-$C_6$ alkenyl, wherein the alkyl or alkenyl moiety may be substituted with one or more halogen atoms or (halo)alkoxy moieties, or $R^3$ is absent when the distal nitrogen atom is part of an imine moiety; and in case the distal nitrogen atom is in cationic form (i.e. the compound is in salt form): $R^4$ is selected from hydrogen (H) or $C_1$-$C_6$ alkyl, wherein the alkyl moiety may be substituted with one or more halogen atoms or (halo)alkoxy moieties and X is an anion, preferably a pharmaceutically acceptable anion; or in case the distal nitrogen atom is in neutral form: $R^4$ and X are absent.

To distinguish between the amide nitrogen atom and the distal nitrogen atom, the latter one is labelled N* in general structure (I). The compound identified by general structure (I) comprises at least one chiral carbon atom (stereocenter), i.e. the atom at the 2-position of the butanoic acid-moiety. Both the compound having an S-configuration as the compound having an R-configuration of the carbon atom at the 2-position are encompassed in the present invention, as well as mixtures of the different stereoisomers. Such a mixture may have one of the configurations in enantiomeric excess, or may be racemic. Whenever one or more additional stereocenters are present in the compound according to the invention, for example in linker L, each may individually exist in the S-configuration, in the R-configuration, or as a mixture of both configurations. Such a mixture may have one of the configurations in enantiomeric excess, or may be racemic. In case addition stereocenters are present, all diastereomers of the compound of general structure (I), in each possible ratio, are encompassed in the present invention.

In a preferred embodiment, the solubility of the compound of the invention in water, expressed as $\log(P_{ow})$ is between 2.0 and 5.0, preferably between 2.5 and 4.5, more preferably between 3.0 and 4.0. $\log(P_{ow})$, the logarithm of the partition coefficient between 1-octanol and water, is a well-known measure of water solubility. Compounds having a $\log(P_{ow})$ value between 3 and 4 are ideally balanced between sufficient water solubility for preparation of aqueous solutions or suspensions and sufficient lipophilicity to ensure efficient transport of the compound over the cellular membrane. The skilled person will appreciate how to determine which combinations of L, $R^1$, $R^2$, $R^3$, $R^4$ and X as defined herein to afford a compound having a $\log(P_{ow})$ value between 3 and 4. Suitable tests to define the $\log(P_{ow})$ value of a compound are well-known to the skilled person, and include but are not limited to the shake-flask method, ITIES, the droplet method or using HPLC. The $\log(P_{ow})$ of a compound can also be predicted using QSPR algorithms.

$R^1$ and $R^2$ are each independently selected from hydrogen (H), $C_1$-$C_6$ alkyl or $C_1$-$C_6$ alkenyl, or one or both of $R^1$ and $R^2$ are embedded in a cyclic structure as described here below. Preferably, $R^1$ is H or $C_1$-$C_2$ alkyl or $R^1$ and $R^2$ are joined together and thus form a second linker between the amide nitrogen atom and the distal nitrogen atom, or $R^1$ is joined with a backbone atom of the linker L in a cyclic structure, more preferably $R^1$ is H or $C_1$-$C_2$ alkyl, even more preferably $R^1$ is H or methyl (Me), most preferably $R^1$ is H. Preferably, $R^2$ is H or $C_1$-$C_2$ alkyl or $R^1$ and $R^2$ are joined together and thus form a second linker between the amide nitrogen atom and the distal nitrogen atom, or $R^2$ is joined with a backbone atom of the linker L in a cyclic structure, more preferably $R^2$ is H or $C_1$-$C_2$ alkyl, even more preferably $R^2$ is H or methyl (Me), most preferably $R^2$ is H. In an especially preferred embodiment, $R^2$ is joined with a backbone atom of the linker L in a saturated cyclic structure, as further defined below, preferably a piperidine ring.

In one embodiment, the amide nitrogen atom is connected to the distal nitrogen atom via a second linker. This second linker is defined by joining together $R^1$ on the amide nitrogen atom and $R^2$ on the distal nitrogen atom. Thus, the amide nitrogen atom, the distal nitrogen atom, the first linker and the second linker together form a cyclic structure, preferably a 4-10-membered cyclic structure, more preferably a 5-8-membered cyclic structure, most preferably a 6-membered cyclic structure. In a preferred embodiment, the second linker is a —$CH_2$—$CH_2$— or —$CH_2$—$CH_2$—$CH_2$— bridge, most preferably a —$CH_2$—$CH_2$— bridge, wherein two or three, preferably two, carbon atoms are present between the amide nitrogen atom and the distal nitrogen atom.

In another embodiment, the amide nitrogen atom is connected to a backbone atom of the linker via a second linker, thereby forming a cyclic structure, preferably a 4-10-membered cyclic structure, more preferably a 5-8-membered cyclic structure, most preferably a 6-membered cyclic structure. The backbone atom of the linker to which the nitrogen atom is connected in this respect has a substituent $R^{1'}$, which is joined together with $R^1$ on the amide nitrogen atom. Thus, the amide nitrogen atom, part of first linker located between the amide nitrogen atom and the atom bearing $R^{1'}$, the backbone atom bearing $R^{1'}$ and the second linker together form the cyclic structure. In this embodiment, the distal nitrogen atom is not included in this cyclic structure, but instead only part of the backbone of the linker is included. In a preferred embodiment, this connection between the amide nitrogen atom and a backbone atom of the linker is a —$CH_2$—$CH_2$— or —$CH_2$—$CH_2$—$CH_2$— bridge, most preferably a —$CH_2$—$CH_2$— bridge, wherein two or three, preferably two, carbon atoms are present between the amide nitrogen atom and the backbone atom of the linker. Most preferably, the cyclic structure containing the amide nitrogen atom is a fully saturated ring, preferably selected from a piperidine ring, a pyrrolidine ring, a piperazine ring, an imidazolidine ring, a pyrazolidine ring and an azepane ring, more preferably a piperidine ring or a pyrrolidine ring, most preferably a piperidine ring.

In another embodiment, the distal nitrogen atom is connected to a backbone atom of the linker via a second linker, thereby forming a cyclic structure, preferably a 4-10-membered cyclic structure, more preferably a 5-8-membered cyclic structure, most preferably a 6-membered cyclic structure. The backbone atom of the linker to which the nitrogen atom is connected in this respect has a substituent $R^{2'}$, which is joined together with $R^2$ on the distal nitrogen atom. Thus, the distal nitrogen atom, part of first linker located between the distal nitrogen atom and the atom bearing $R^{2'}$, the backbone atom bearing $R^{2'}$ and the second linker together form the cyclic structure. In this embodiment, the amide nitrogen atom is not included in this cyclic structure, but instead only part of the backbone of the linker is included. In a preferred embodiment, this connection between the distal nitrogen atom and a backbone atom of the linker is a —$CH_2$—$CH_2$— or —$CH_2$—$CH_2$—$CH_2$— bridge, most preferably a —$CH_2$—$CH_2$— bridge, wherein two or three, preferably two, carbon atoms are present between the distal nitrogen atom and the backbone atom of the linker. Most preferably, the cyclic structure containing the distal nitrogen atom is a fully saturated ring, preferably selected from a piperidine ring, a pyrrolidine ring, a piperazine ring, an imidazolidine ring, a pyrazolidine ring and an azepane ring, more preferably a piperidine ring or a pyrrolidine ring, most preferably a piperidine ring. It is also possible that a connection exists between $R^1$ on the amide nitrogen atom and an $R^{1'}$ substituent on the linker and between $R^2$ on the distal nitrogen atom and an $R^{2'}$ substituent on the linker.

Among the above-mentioned possibilities for $R^2$, it is most preferred that the distal nitrogen atom is connected to a backbone atom of the linker via a second linker wherein $R^2$ is joined with $R^{2'}$, as further defined here above. Among the tested compounds, these have been found most active.

When the distal nitrogen atom is part of an imine moiety, the linker L comprises at least one double bond located between the distal nitrogen atom and the adjacent backbone atom of the linker, or $R^2$ comprises at least one double bond located between the distal nitrogen atom and the adjacent atom of $R^2$ (i.e. $R^2=C_1$-$C_6$ alkenyl). In such instances, $R^3$ is absent. In the context of the present invention, the distal nitrogen being part of an imine moiety includes instances wherein the distal nitrogen atom is part of an heteroaromatic ring, in particular a pyrrole ring, a pyridine ring or a imidazole ring, in which instances a double bond is formally present between the distal nitrogen atom and the adjacent carbon atom either in the linker or in $R^2$. Preferred moieties comprising an imine moiety include guanidine, amidine and pyridine. For guanidine and amidine, one of the nitrogen atoms is substituted to form the connection with the amide nitrogen atom via linker L. For pyridine, one of the carbon atoms is substituted. When the distal nitrogen atom is part of an amine moiety, it is connected to the linker and $R^2$ via two single bonds, and $R^3$ is present. It is preferred that the distal nitrogen atom is part of an amine moiety, i.e. having three or four single bonds to each of $R^1$, $R^2$, $R^3$ and optionally $R^4$.

In the instance that $R^3$ is present, $R^3$ is selected from hydrogen (H), $C_1$-$C_6$ alkyl or $C_1$-$C_6$ alkenyl, wherein the alkyl or alkenyl moiety may be substituted with one or more halogen atoms or (halo)alkoxy moieties, preferably $R^3$ is H or $C_1$-$C_6$ alkyl, more preferably $R^3$ is H or $C_1$-$C_4$ alkyl, even more preferably $R^3$ is H or $C_1$-$C_2$ alkyl, wherein the alkyl moiety may be substituted with one or more halogen atoms or (halo)alkoxy moieties. Halogen atoms include fluorine (F), chlorine (Cl), bromine (Br), iodine (I), and astatine (At), preferably the halogen atom is fluorine (F). Preferred alkoxy moieties include methoxy and ethoxy. In haloalkoxy moieties, at least one hydrogen atom of an alkoxy moiety is replaced by a halogen atom, preferably by F. Suitable moieties for $R^3$ include, preferably are limited to, H, methyl (Me), trifluoromethyl (—$CF_3$), ethyl (Et), isopropyl (iPr), cyclopropyl (-cPr), methylene cyclopropyl (—$CH_2cPr$), n-propyl (n-Pr), 2,2,2-trifluoroethyl (—$CH_2CF_3$) and methoxymethyl (—$CH_2OCH_3$), more preferably $R^3$ is H or methyl (Me), most preferably $R^3$ is H. Alternatively, $R^3$ is preferably $C_1$-$C_4$ alkyl, wherein the alkyl moiety may be substituted with one or more halogen atoms or (halo)alkoxy moieties, more preferably $R^3$ is $C_1$-$C_2$ alkyl, wherein the alkyl moiety may be substituted with one or more halogen atoms or (halo)alkoxy moieties.

Distal nitrogen atom N* may be in neutral or in cationic form. In a first preferred embodiment, the distal nitrogen atom is in neutral form, in which case both $R^4$ and X are absent. In an alternative preferred embodiment, the distal nitrogen atom is in cationic form, in which case both $R^4$ and X are present as defined herein.

In case the distal nitrogen atom is in cationic form, it formally originates from protonation or alkylation, preferably protonation or methylation of a trivalent nitrogen atom. The trivalent nitrogen atom is preferably an amine moiety, either primary, secondary or tertiary, or an imine moiety, either primary or secondary. The counter ion (X) of the cationic distal nitrogen atom is a negatively charged ion, preferably a monovalent negatively charged ion, more preferably an anion as indicated herein below. The synthesis of the compounds of the invention does not need to encompass the protonation or alkylation of an amine or imine nitrogen atom. The cationic distal nitrogen atom may also be formed via a different route. As such, the cationic distal nitrogen atom only "formally" originates from the protonation or alkylation of an amine or imine nitrogen atom.

$R^4$ is the substituent on the cationic distal nitrogen atom, which originates from formal protonation or alkylation of the amine or imine moiety. Thus, the compound according to this embodiment, in view of the presence of the cationic nitrogen atom and X, is a salt, preferably a pharmaceutically acceptable salt. Pharmaceutically acceptable salts are those salts that are suitable to be administered as drugs or pharmaceuticals to humans and/or animals. The pharmaceutically acceptable salts of the amine or imine moiety of the compound according to the invention are known to those skilled in the art, and originate from formal treatment of the compound with an acid (protonation agent) or an alkylating agent. Suitable acids include organic acids or inorganic acids. Examples of inorganic acids include, but are not limited to, hydrochloric acid (HCl), hydrobromic acid (HBr), hydroiodic acid (HI), sulphuric acid ($H_2SO_4$), nitric acid ($HNO_3$), trifluoroacetic acid (TFAH or $CF_3CO_2H$) and phosphoric acid ($H_3PO_4$). Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids and salicylic acid. When an acid as exemplified here is used to formally prepare the salt, $R^4$ is hydrogen, and the type of acid determines counter ion X. Alternatively, the salt can be formed by formal treatment with an alkylating agent. Suitable alkylating agents include, but are not limited to, $C_1$-$C_6$ alkyl halides (such as methyl iodide, ethyl iodide, propyl iodide, butyl chloride, butyl fluoride, butyl bromide), dimethyl sulphate, dimethyl carbonate, methyl triflate, methyl fluorosulfonate, methyl chlorosulfonate, methyl methanesulfonate and methyl benzenesulfonate. The salt may be prepared by actual treatment of the non-salt compound with an acid or alkylation agent, as indicated above, or via other means known in the art and/or exemplified further below.

$R^4$ is selected from hydrogen (H) or $C_1$-$C_6$ alkyl, wherein the alkyl moiety may be substituted with one or more halogen atoms or (halo)alkoxy moieties, preferably $R^4$ is H or $C_1$-$C_4$ alkyl, wherein the alkyl moiety may be substituted with one or more halogen atoms or (halo)alkoxy moieties, more preferably $R^4$ is H or $C_1$-$C_2$ alkyl, wherein the alkyl moiety may be substituted with one or more halogen atoms or (halo)alkoxy moieties. Halogen atoms include fluorine (F), chlorine (Cl), bromine (Br), iodine (I), and astatine (At), preferably the halogen atom is fluorine (F). Preferred alkoxy moieties include methoxy and ethoxy. In haloalkoxy moieties, at least one hydrogen atom of an alkoxy moiety is replaced by a halogen atom, preferably by F. Suitable moieties for $R^4$ include, preferably are limited to, H, methyl (Me), trifluoromethyl (—$CF_3$), ethyl (Et), isopropyl (iPr), cyclopropyl (-cPr), methylene cyclopropyl (—$CH_2cPr$), n-propyl (n-Pr), 2,2,2-trifluoroethyl (—$CH_2CF_3$), methoxymethyl (—$CH_2OCH_3$). Even more preferably $R^4$ is H or methyl (Me), most preferably $R^4$ is H.

X can be any anion, preferably a physiologically or pharmaceutically acceptable anion, more preferably a monovalent anion. X is preferably selected from F, Cl, Br, I, $HSO_4$, $NO_3$, TFA ($CF_3CO_2$), formate, acetate, propionate, glycolate, pyruvate, oxalate, maleate, malonate, succinate, fumarate, tartarate, citrate, benzoate, cinnamate, mandelate, sulfonate and salicylate. Preferably, X is Cl, I, TFA or formate, more preferably Cl, I, TFA or formate, even more preferably X is Cl or formate, most preferably X is Cl. When the cationic nitrogen atom originates from formal protonation, this protonation is preferably accomplished with hydrogen chloride (HCl), trifluoroacetic acid (TFAH or $CF_3CO_2H$) or formic acid (HCOOH), more preferably with HCl or formic acid. Formal methylation is preferably accomplished with methyl iodide (MeI). Thus, in a preferred embodiment, $R^4$=Me when X=I$^-$, and $R^4$=H when X=Cl$^-$, TFA$^-$ or formate.

In an especially preferred embodiment, the distal nitrogen atom is neutral and $R^2$ is joined with a backbone atom of the linker L in a cyclic structure as further defined above, preferably a saturated cyclic structure, most preferably a piperidine ring.

Appropriate linkers L to connect the amide nitrogen atom to the distal nitrogen atom are linkers preferably comprising 1 to 10 optionally substituted backbone atoms more preferably comprising 1 to 8 optionally substituted backbone atoms. L can thus comprise 1, 2, 3, 4, 5, 6, 7, 8, 9 or 10 optionally substituted backbone atoms. Herein, backbone atoms are those atoms that make up the shortest chain between the amide nitrogen atom and the distal nitrogen atom. The backbone may be a linear structure, but may also be part of a cyclic structure. When the backbone is part a cyclic structure, the backbone is defined as the shortest chain between the amide nitrogen atom and the distal nitrogen atom. In such instances, one of the backbone atoms comprises a substituent $R^5$, and one of the backbone atoms comprises a substituent $R^{5'}$, preferably two different backbone atoms comprise the substituents $R^5$ and $R^{5'}$, wherein $R^5$ and $R^{5'}$ are joined to form a cyclic structure, preferably a 4-10-membered cyclic structure, more preferably a 5-8-membered cyclic structure, most preferably a 6-membered cyclic structure. In this embodiment, the amide nitrogen atom and the distal nitrogen atom are not included in the cyclic structure, but instead only part of the backbone of the linker is included. In a preferred embodiment, this connection between the backbone atom(s) of the linker, bearing the $R^5$ and $R^{5'}$ substituents, is a —$(CH_2)_n$— bridge, wherein n=1-6, preferably a —$CH_2$—$CH_2$— or —$CH_2$—$CH_2$—$CH_2$— bridge, wherein one to six, preferably two or three, carbon atoms are present between the substituted backbone atom(s) of the linker.

In a preferred embodiment, the backbone atoms are selected from carbon, nitrogen and oxygen, preferably from carbon and nitrogen. Such a backbone according to this preferred embodiment may be identified as $C_{n-m}N_m$, wherein n designates the total number of atoms in the backbone, and m the number of nitrogen atoms in the backbone. Each of n and m is a non-negative integer. Suitable linkers have n=1-10 and m=0-4, preferably n=2-7 and m=0-3, more preferably n=4-7 and m=0-2. Especially preferred linkers have a backbone identified as $C_{n-m}N_m$, wherein n=2 and m=0 ($C_2$); n=5 and m=1 ($C_4N$); n=3 and m=0 ($C_3$); n=4 and m=1 ($C_3N$); n=7 and m=2 ($C_5N_2$); n=4 and m=0 ($C_4$); n=6 and m=1 ($C_5N$); or n=5 and m=0 ($C_5$). Most preferably, all backbone atoms are carbon atoms (m=0).

To fulfil their valence requirements, the carbon and nitrogen backbone atoms of the linker may bear hydrogen atoms, may be substituted, or double or triple bonds may be present between adjacent backbone atoms, as will be understood by the skilled person. In the context of the invention, hydrogen is not regarded a substituent. Whenever an oxygen atom is present as backbone atom in the linker, the skilled person will understand that the oxygen backbone atom bears no hydrogen atoms, substituents or double or triple bonds. Triple bonds may be present between two carbon atoms of the backbone. The backbone atoms, together with the hydrogen atoms and/or the substituents, constitute the linker. In the context of the present invention, "optionally substituted" is used to indicate that an (backbone) atom may bear one or more substituents, or may bear no substituents and sufficient hydrogen may be present instead, to fulfil the valence requirements of said (backbone) atom.

Suitable substituents include but are not limited to halogen, $NH_2$, $NHR^6$, $N(R^6)_2$, $NHNH_2$, $N_3$, NHC(=O)$R^6$, NHC(=O)NH$R^6$, NHC(=O)$NH_2$, NHC(=O)O$R^6$, OH, O$R^6$, OC(=O)$R^6$, $R^6$ (e.g. alkyl, cycloalkyl), aralkyl, alkenyl, alkynyl, aryl, heteroaryl, OC(=O)O$R^6$, OC(=O)N$R^6$, O(SO$_2$)$R^6$, O(SO$_2$)OH, O(PO$_2$)OH, SH, S$R^6$, C(=O)$R^6$, alkyl-$NH_2$, alkyl-OH, alkyl-SH, C(=O)$CF_3$, C(=O)O$R^6$, C(=O)OH, C(=O)H, C(=O)O$R^6$, C(=O)$NH_2$, C(=O)$NMe_2$, C(=O)N($R^6$)$_2$, C(=S)$NH_2$ C(=S)SH, CN, NC, CNO, ONC, OCN, SCN, SNC, CNS, S(=O)$R^6$, S(=O)$_2R^6$, S(=O)$_2$(OH), P(=O)(OH)$_2$ or P(=O)(OH)(O$R^6$). Atoms having two or more remaining valencies, such as carbon backbone atoms, may bear a double bonded substituent, such as oxo (=O), imino (=NH or =NRW), thioxo (=S), alkylidene (=$CH_2$ or =CH$R^6$ or =C($R^6$)$_2$). In addition, two substituents on the same atom or on different atoms may be joined to form cyclic structures. If two substituents on a single backbone atom are joined in a cyclic structure, this cyclic structure may be regarded as being connected via a spiro junction to the backbone. If two substituents on different backbone atoms are joined in a cyclic structure, part of this cyclic structure is (part of) the backbone, and the backbone is considered to be the shortest chain of atoms between the amide nitrogen atom and the distal nitrogen atom. As further indicated below, a cyclic structure may also be formed by joining one substituent on a backbone atom with $R^1$ on the amide nitrogen atom or with $R^2$ on the distal nitrogen atom. The cyclic structures formed as such may be all-carbon or may comprise 0-3 heteroatoms (e.g. N, O, S and/or P), and may comprise 0-3 double bonds. All atoms in these cyclic structures may optionally be substituted. Examples of suitable cyclic structures are optionally substituted cycloalkyl, optionally substituted cycloheteroalkyl, optionally substituted aryl or optionally substituted heteroaryl. Here above, each $R^6$ is independently an alkyl moiety, preferably a $C_1$-$C_6$ alkyl moiety, more preferably a $C_1$-$C_2$ alkyl moiety. Within $R^6$, one or more $CH_2$ moieties may each independently be replaced by one of O, S or NH, and/or one or more CH moieties may be replaced by N.

In the context of the present invention, the term "alkyl" refers to saturated aliphatic groups including straight-chain, branched-chain, cyclic groups, and combinations thereof, having the number of carbon atoms specified, or if no number is specified, preferably having up to 12 carbon atoms. "Straight-chain alkyl" or "linear alkyl" group refers to alkyl groups that are neither cyclic nor branched, commonly designated as "n-alkyl" groups. One subset of alkyl groups is $C_1$-$C_6$ alkyl, which includes groups such as methyl, ethyl, n-propyl, isopropyl, butyl, n-butyl, isobutyl, sec-butyl, t-butyl, pentyl, n-pentyl, hexyl, cyclopropyl, cyclobutyl, cyclopentyl, cyclohexyl, and any other alkyl group containing between one and six carbon atoms, where the $C_1$-$C_6$ alkyl groups can be attached via any valence on the $C_1$-$C_6$ alkyl groups.

Preferred substituents of the backbone atoms are alkyl, such as methyl (Me or —$CH_3$), carboxy (—C(=O)OH), oxo (=O) and primary amino (—NH).

Preferred linkers are identified here below as $L^1$ to $L^{26}$:

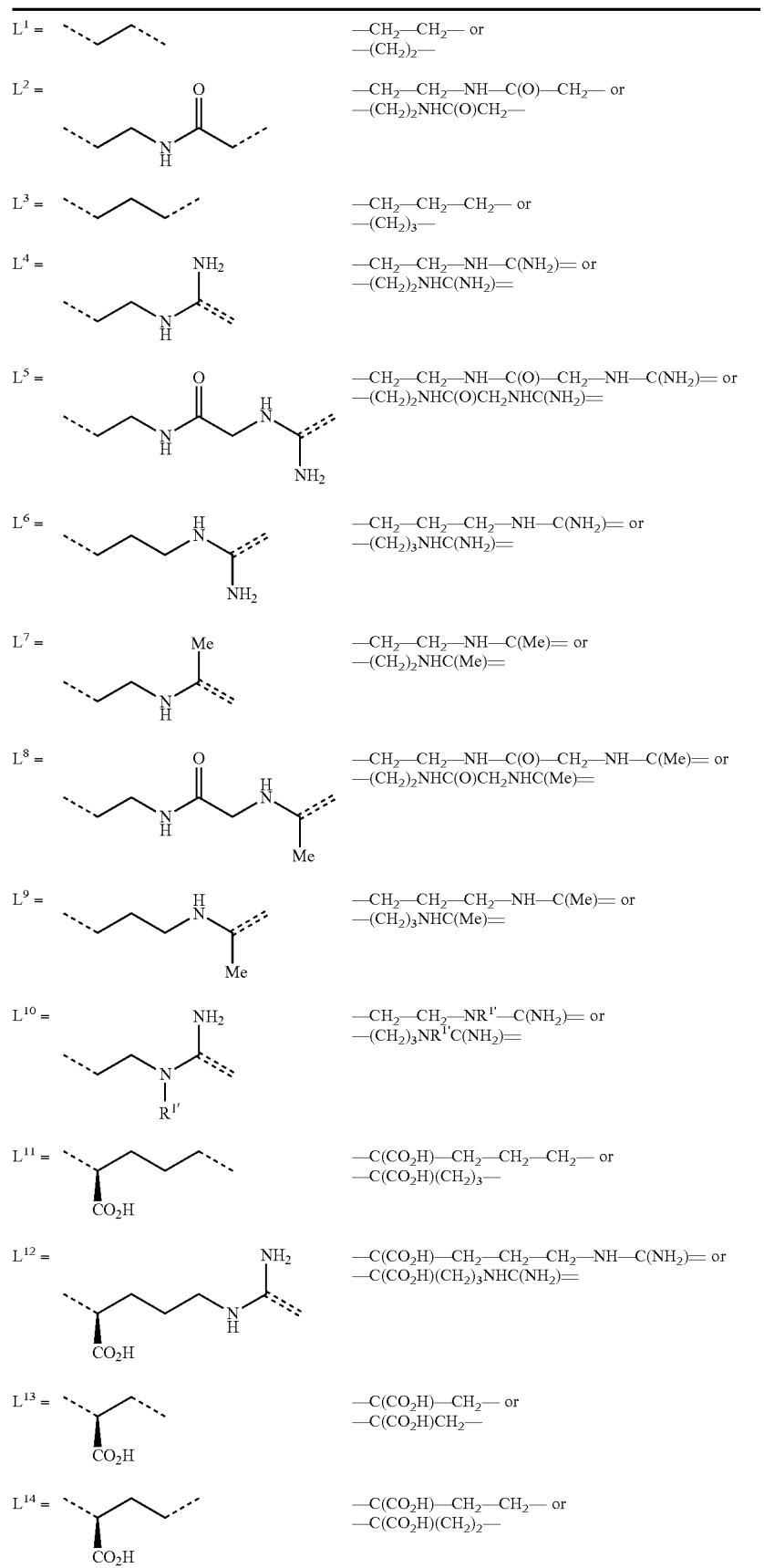

| | | |
|---|---|---|
| L¹ = | (CH₂CH₂) | —CH₂—CH₂— or<br>—(CH₂)₂— |
| L² = | CH₂CH₂NHC(O)CH₂ | —CH₂—CH₂—NH—C(O)—CH₂— or<br>—(CH₂)₂NHC(O)CH₂— |
| L³ = | (CH₂)₃ | —CH₂—CH₂—CH₂— or<br>—(CH₂)₃— |
| L⁴ = | CH₂CH₂NHC(NH₂)= | —CH₂—CH₂—NH—C(NH₂)= or<br>—(CH₂)₂NHC(NH₂)= |
| L⁵ = | | —CH₂—CH₂—NH—C(O)—CH₂—NH—C(NH₂)= or<br>—(CH₂)₂NHC(O)CH₂NHC(NH₂)= |
| L⁶ = | | —CH₂—CH₂—CH₂—NH—C(NH₂)= or<br>—(CH₂)₃NHC(NH₂)= |
| L⁷ = | | —CH₂—CH₂—NH—C(Me)= or<br>—(CH₂)₂NHC(Me)= |
| L⁸ = | | —CH₂—CH₂—NH—C(O)—CH₂—NH—C(Me)= or<br>—(CH₂)₂NHC(O)CH₂NHC(Me)= |
| L⁹ = | | —CH₂—CH₂—CH₂—NH—C(Me)= or<br>—(CH₂)₃NHC(Me)= |
| L¹⁰ = | | —CH₂—CH₂—NR¹'—C(NH₂)= or<br>—(CH₂)₃NR¹'C(NH₂)= |
| L¹¹ = | | —C(CO₂H)—CH₂—CH₂—CH₂— or<br>—C(CO₂H)(CH₂)₃— |
| L¹² = | | —C(CO₂H)—CH₂—CH₂—CH₂—NH—C(NH₂)= or<br>—C(CO₂H)(CH₂)₃NHC(NH₂)= |
| L¹³ = | | —C(CO₂H)—CH₂— or<br>—C(CO₂H)CH₂— |
| L¹⁴ = | | —C(CO₂H)—CH₂—CH₂— or<br>—C(CO₂H)(CH₂)₂— |

-continued

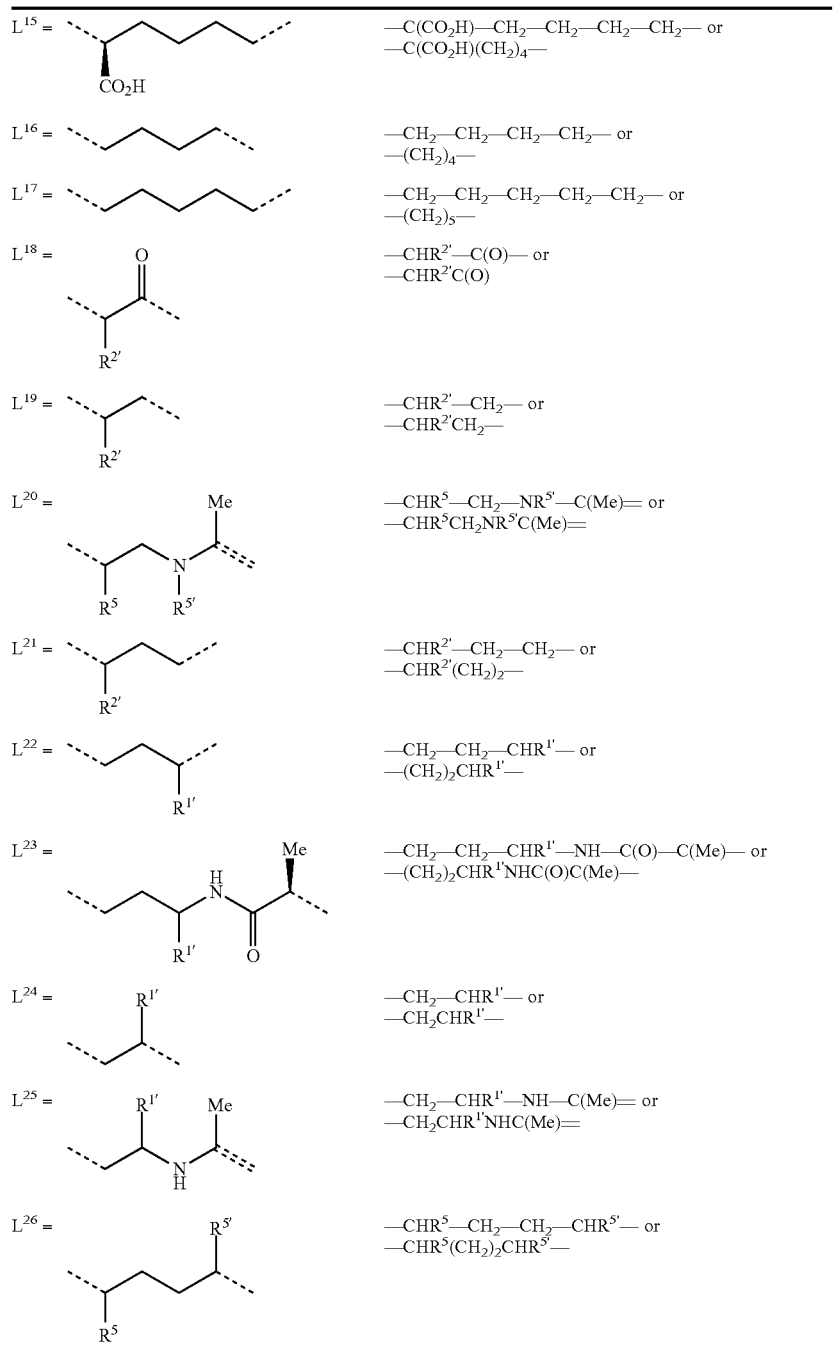

Herein, the dashed bond at the left side of each of the structures for $L^1$ to $L^{26}$ indicates the bond between the linker and the amide nitrogen atom, and the dashed bond at the right side of each of the structures for $L^1$ to $L^{26}$ indicates the bond between the linker and the distal nitrogen atom. The linkers depicted as chemical formulas are oriented in the same direction, i.e. the pendant bond at the left side of each of the chemical formulas for $L^1$ to $L^{26}$ indicates the bond between the linker and the amide nitrogen atom, and the dashed bond at the right side of each of the chemical formulas for $L^1$ to $L^{26}$ indicates the bond between the linker and the cationic nitrogen atom.

Each occurrence of $R^{1'}$ represents the connection of a second linker between the linker and the amide nitrogen atom, wherein $R^{1'}$ is joined with $R^1$ via said bridge, thus forming a 4-10-membered cyclic structure, preferably a 5-8-membered cyclic structure, most preferably a 6-membered cyclic structure, which is built up from the amide nitrogen atom, 1-4 atoms of the backbone of the linker, and 1-4 atoms which make up the bridge joining $R^1$ and $R^{1'}$. Likewise, each occurrence of $R^{2'}$ represents the connection of a second linker between the linker and the cationic nitrogen atom, wherein $R^{2'}$ is joined with $R^2$ via said bridge, thus forming a 4-10-membered cyclic structure, preferably a 5-8-membered cyclic structure, most preferably a 6-membered cyclic structure, which is built up from the cationic nitrogen atom, 1-4 atoms of the backbone of the linker, and 1-4 atoms which make up the bridge joining $R^2$ and $R^{2'}$. Likewise, each occurrence of $R^5$ and $R^{5'}$ represent the connection of a second linker between one backbone atom of the linker, bearing $R^5$, and another backbone atom of the linker, bearing $R^{5'}$, wherein $R^{5'}$ is joined with $R^5$ via said bridge, thus forming a 4-10-membered cyclic structure, preferably a 5-8-membered cyclic structure, most preferably a 6-membered cyclic structure, which is built up from 2-5 atoms of the backbone of the linker, and 1-5 atoms which make up the bridge joining $R^5$ and $R^{5'}$. Thus, in linkers $L^{10}$, $L^{22}$, $L^{23}$, $L^{24}$ and $L^{25}$, $R^{1'}$ is joined to $R^1$ via a second linker, preferably a —CH$_2$—CH$_2$— or —CH$_2$—CH$_2$—CH$_2$— bridge, more preferably a —CH$_2$—CH$_2$-bridge. Thus, in a compound comprising linker $L^{10}$, wherein $R^{1'}$ and $R^1$ are joined via a —CH$_2$—CH$_2$— bridge, the amide nitrogen atom is embedded in a six-membered cyclic structure, which is built up from the amide nitrogen atom, two carbon atoms and one nitrogen atom of the backbone of the linker, and two more carbon atoms which make up the bridge of $R^1$ and $R^{1'}$. This —CH$_2$—CH$_2$— bridge between the amide nitrogen atom and the central nitrogen atom in the backbone of linker $L^{10}$ may be represented as L. Likewise, in linkers $L^{18}$, $L^{19}$ and $L^{21}$, $R^2$ is joined to $R^{2'}$ via a second linker, preferably a —CH$_2$—CH$_2$— or —CH$_2$—CH$_2$—CH$_2$— bridge, more preferably a —CH$_2$—CH$_2$—CH$_2$— bridge. Likewise, in linker $L^{20}$ and $L^{26}$, $R^{5'}$ is joined to $R^5$ via a second linker, preferably a —CH$_2$—CH$_2$— or —CH$_2$—CH$_2$—CH$_2$— bridge, more preferably a —CH$_2$—CH$_2$— bridge.

Linkers $L^{11}$, $L^{12}$, $L^{13}$, $L^{14}$, $L^{15}$, $L^{16}$ (as long as $R^2$-$R^{2'}$ is not —C(O)—), $L^{19}$ (as long as $R^2$-$R^{2'}$ is not —CH$_2$—), $L^{20}$ (as long as $R^5$-$R^{5'}$ is not —CH$_2$—), $L^{2'}$ (as long as $R^2$-$R^{2'}$ is not —CH$_2$—CH$_2$—), $L^{22}$ (as long as $R^1$-$R^{1'}$ is not —CH$_2$—CH$_2$—), $L^{23}$ (as long as $R^1$-$R^{1'}$ is not —CH$_2$—CH$_2$—), $L^{24}$ (as long as $R^1$-$R^{1'}$ is not —CH$_2$—) and $L^{25}$ (as long as $R^1$-$R^{1'}$ is not —CH$_2$—) comprise an additional stereocenter. The stereoisomer, when indicated in the structures of those linkers, above is meant as illustrative, not as limiting. As indicated further above, each stereocenter present in the compounds according to the invention may individually be present in each of its stereoisomeric forms, either S or R, or as a mixture of both isomers in any ratio. Linker $L^{26}$ comprises a disubstituted cycloalkyl moiety, preferably a disubstituted cyclohexyl moiety, and may thus occur in either the cis-form or the trans-form, preferably in the trans-form.

Especially preferred linkers are $L^5$, $L^8$, $L^{11}$, $L^{12}$, $L^{16}$, $L^{17}$, $L^{19}$, $L^{21}$ and $L^{26}$. Even more preferred linkers are L, $L^{16}$, $L^{19}$ and $L^{26}$, and most preferably the linker is $L^{19}$. Preferably, $L^{19}$ is combined with $R^2$-$R^{2'}=L^1$ or $L^3$, most preferably with $R^2$-$R^{2'}=L^3$. Preferably, $L^{21}$ is combined with $R^2$-$R^{2'}=L^1$ or $L^3$, most preferably with $R^2$-$R^{2'}=L^1$. Preferably, $L^{26}$ is combined with $R^5$-$R^{5'}=L^1$ or $L^3$, more preferably with $R^5$-$R^{5'}=L^1$, most preferably wherein the cyclohexyl is trans-1,4-disubstituted. Especially preferred is the combination of linker $L^{19}$ with $R^2$-$R^{2'}=L^3$ and $R^3$=H, Me, Et, iPr, CH$_2$OCH$_3$ or CH$_2$CF$_3$, more preferably $R^3$=Me, Et, iPr or CH$_2$CF$_3$, most preferably $R^3$=H In case $R^4$ and X are absent, it is preferred that linker L contains 1-5 optionally substituted backbone atoms and/or linker L contains at least one backbone atom other than carbon. In case $R^4$ and X are absent, it is especially preferred that the distal nitrogen atom is connected to a backbone atom of the linker via a second linker wherein $R^2$ is joined with $R^{2'}$, more preferably wherein the cyclic structure thus formed is a piperidine ring, a pyrrolidine ring, an imidazolidine ring, a pyrazolidine ring or an azepane ring, most preferably a piperidine ring, and/or at least one of the backbone atoms is substituted with a carboxylic acid moiety. In case $R^4$ and X are absent, it is especially preferred that L is any one of $L^2$, $L^4$-$L^{21}$, $L^{23}$, $L^{25}$ and $L^{26}$, more preferably one of $L^5$, $L^8$, $L^{11}$, $L^{12}$, $L^{16}$, $L^{17}$, $L^{19}$, $L^{21}$ and $L^{26}$.

In case $R^4$ and X are present, it is preferred that $R^4$ is H or Me, more preferably $R^4$ is H, and X is Cl, I, TFA or formate, even more preferably X is Cl or formate, most preferably X is Cl. In case $R^4$ and X are present, it is preferred that linker L contains 3-10 backbone atoms, or 2 backbone atoms of which one is connected to the distal nitrogen atom via a second linker. In case $R^4$ and X are present, it is especially preferred that L is any one of $L^2$-$L^{26}$, more preferably one of $L^5$, $L^8$, $L^{11}$, $L^{12}$, $L^{16}$, $L^{17}$, $L^{19}$, $L^{21}$ and $L^{26}$.

In one preferred embodiment, the compound according to the invention is represented by general structure (I), wherein
L is a linker between the amide nitrogen atom and the distal nitrogen atom;
$R^1$ is selected from hydrogen (H), $C_1$-$C_6$ alkyl or $C_1$-$C_6$ alkenyl, or $R^1$ is joined with a backbone atom of the linker L in a cyclic structure;
$R^2$ is joined with a backbone atom of the linker L to form a cyclic structure selected from a piperidine ring, a pyrrolidine ring, an imidazolidine ring, a pyrazolidine ring or an azepane ring;
$R^3$ is selected from hydrogen (H), $C_1$-$C_6$ alkyl or $C_1$-$C_6$ alkenyl, wherein the alkyl or alkenyl moiety may be substituted with one or more halogen atoms or (halo) alkoxy moieties, or $R^3$ is absent when the distal nitrogen atom is part of an imine moiety; and
$R^4$ and X are absent.

In an alternative preferred embodiment, the compound according to the invention is represented by general structure (I), wherein
L is a linker between the amide nitrogen atom and the distal nitrogen atom comprising 3-10 backbone atoms, or 2 backbone atoms of which one is connected to the distal nitrogen atom via a second linker;
$R^1$ and $R^2$ are each independently selected from hydrogen (H), $C_1$-$C_6$ alkyl or $C_1$-$C_6$ alkenyl, or $R^1$ and $R^2$ are joined together and thus form a second linker between the amide nitrogen atom and the distal nitrogen atom, or $R^1$ is joined with a backbone atom of the linker L in a cyclic structure and/or $R^2$ is joined with a backbone atom of the linker L in a cyclic structure;
$R^3$ is selected from hydrogen (H), $C_1$-$C_6$ alkyl or $C_1$-$C_6$ alkenyl, wherein the alkyl or alkenyl moiety may be substituted with one or more halogen atoms or (halo) alkoxy moieties, or $R^3$ is absent when the distal nitrogen atom is part of an imine moiety;
$R^4$ is selected from hydrogen (H) or $C_1$-$C_6$ alkyl, wherein the alkyl moiety may be substituted with one or more halogen atoms or (halo)alkoxy moieties; and
X is an anion, preferably a pharmaceutically acceptable anion.

Preferred compounds according to the invention are identified here below as compounds A to AH, which are defined by general structure (I), wherein:
for compound A: L=$L^1$, $R^1$-$R^2$=$L^1$, $R^3$=H;
for compound B: L=$L^1$, $R^1$=H, $R^2$=H, $R^3$=H;
for compound C: L=$L^2$, $R^1$=H, $R^2$=H, $R^3$=H;
for compound D: L=$L^3$, $R^1$=H, $R^2$=H, $R^3$=H;
for compound E: L=$L^4$, $R^1$=H, $R^2$=H, $R^3$=absent;
for compound F: L=$L^5$, $R^1$=H, $R^2$=H, $R^3$=absent;
for compound G: L=$L^6$, $R^1$=H, $R^2$=H, $R^3$=absent;

for compound H: $L=L^3$, $R^1=H$, $R^2=Me$, $R^3=Me$;
for compound I: $L=L^1$, $R^1=H$, $R^2=Me$, $R^3=Me$;
for compound J: $L=L^7$, $R^1=H$, $R^2=H$, $R^3=$absent;
for compound K: $L=L^8$, $R^1=H$, $R^2=H$, $R^3=$absent;
for compound L: $L=L^9$, $R^1=H$, $R^2=H$, $R^3=$absent;
for compound M: $L=L^{10}$, $R^1$-$R^{1'}=L^1$, $R^2=H$, $R^3=$absent;
for compound N: $L=L^{11}$, $R^1=H$, $R^2=H$, $R^3=H$;
for compound O: $L=L^{12}$, $R^1=H$, $R^2=H$, $R^3=$absent;
for compound P: $L=L^{13}$, $R^1=H$, $R^2=H$, $R^3=H$;
for compound Q: $L=L^{14}$, $R^1=H$, $R^2=H$, $R^3=H$;
for compound R: $L=L^{15}$, $R^1=H$, $R^2=H$, $R^3=H$;
for compound S: $L=L^{11}$, $R=H$, $R^2=Me$, $R^3=Me$
for compound T: $L=L^{16}$, $R=H$, $R^2=H$, $R^3=H$;
for compound U: $L=L^{17}$, $R=H$, $R^2=H$, $R^3=H$;
for compound V: $L=L^{16}$, $R=H$, $R^2=Me$, $R^3=Me$;
for compound W: $L=L^{18}$, $R^1=H$, $R^2$-$R^{2'}=L^3$, $R^3=H$;
for compound X: $L=L^{19}$, $R^1=H$, $R^2$-$R^{2'}=L^3$, $R^3=H$;
for compound Y: $L=L^{20}$, $R=H$, $R^2=H$, $R^5$-$R^{5'}=L^3$, $R^3=$absent;
for compound Z: $L=L^{21}$, $R^1=H$, $R^2$-$R^{2'}=L^1$, $R^3=H$;
for compound AA: $L=L^{22}$, $R^1$-$R^{1'}=L$, $R^2=H$, $R^3=H$;
for compound AB: $L=L^{23}$, $R^1$-$R^{1'}=L^1$, $R^2=H$, $R^3=H$;
for compound AC: $L=L^{24}$, $R^1$-$R^{1'}=L^3$, $R^2=H$, $R^3=H$;
for compound AD: $L=L^{25}$, $R^1$-$R^{1'}=L^3$, $R^2=H$, $R^3=$absent;
for compound AE: $L=L^{26}$, $R^1=H$, $R^2=H$, $R^5$-$R^{5'}=L^1$, $R^3=H$.
for compound AF: $L=L^{19}$, $R^1=H$, $R^2$-$R^{2'}=L^3$, $R^3=Me$;
for compound AG: $L=L^{19}$, $R^1=H$, $R^2$-$R^{2'}=L^1$, $R^3=H$;
for compound AH: $L=L^{21}$, $R^1=H$, $R^2$-$R^{2'}=L^1$, $R^3=Me$.

Herein, $R^4$ and X may either be present or absent. In case $R^4$ and X are absent, it is especially preferred that the compound according to the invention is selected from compounds A-F and J-AH. In case $R^4$ and X are present, it is especially preferred that the compound according to the invention is selected from compounds A-H and J-AH, more preferably wherein $R^4=H$ and $X=Cl$ or formate, most preferably wherein $R^4=H$ and $X=Cl$.

Especially preferred compounds according to the invention are compounds F, K, N, O, U, V, T, X, Z, AE, AF, AG and AH, more preferably N, T, X and AE, most preferably X.

Compound F may have the R-configuration, the S-configuration or a mixture thereof, preferably compound F is a mixture of the R- and S-enantiomers, more preferably a racemic mixture. Compound K may have the R-configuration, the S-configuration or a mixture thereof, preferably compound K is a mixture of the R- and S-enantiomers, more preferably a racemic mixture. Compound N may have the R,R-configuration, R,S-configuration, S,R-configuration, the S,S-configuration or any mixture thereof, preferably compound N has the R,R-configuration or the S,R-configuration, most preferably the R,R-configuration. Compound O may have the R,R-configuration, R,S-configuration, S,R-configuration, the S,S-configuration or any mixture thereof, preferably compound O is a mixture of the R,S- and S,S-diastereomers more preferably about 1/1 (mol/mol) mixture. Compound U may have the R-configuration, the S-configuration or a mixture thereof, preferably compound U has the R-configuration or the S-configuration. Compound V may have the R-configuration, the S-configuration or a mixture thereof, preferably compound V has the R-configuration. Compound T may have the R-configuration, the S-configuration or a mixture thereof, preferably compound T has the R-configuration or the S-configuration, most preferably the R-configuration. Compound X may have the R,R-configuration, R,S-configuration, S,R-configuration, the S,S-configuration or any mixture thereof, preferably compound X has the R,S-configuration or the S,R-configuration, most preferably the S,R-configuration. Compound Z may have the R-configuration, the S-configuration or a mixture thereof, preferably compound Z is a mixture of the R- and S-enantiomers, more preferably a racemic mixture. Compound AE may have the R,trans-configuration, R,cis-configuration, S,trans-configuration, the S,cis-configuration or any mixture thereof, preferably compound AE has the R,trans-configuration or the S,trans-configuration, most preferably the R,trans-configuration. Compound AF may have the R,R-configuration, R,S-configuration, S,R-configuration, the S,S-configuration or any mixture thereof, preferably compound AF has the S,R-configuration. Compound AG may have the R,R-configuration, R,S-configuration, S,R-configuration, the S,S-configuration or any mixture thereof, preferably compound AG has the S,S-configuration or the S,R-configuration. Compound AH may have the R-configuration, the S-configuration or a mixture thereof, preferably compound AH has the S-configuration. Herein, the first designator (R or S) of the configuration is for the 2-position of the open-Trolox moiety, and in case an additional stereocenter is present in the compound according to the invention, the second designator thereof defines the configuration.

The most preferred compounds according to the invention are compound N in the R,R-configuration (R,R—N), compound T in the R-configuration (R-T), compound AE in the R,trans-configuration (R,trans-AE) and compound X in any configuration, most preferably the compound according to the invention is compound X in the S,R-configuration (S,R—X). In one embodiment, these most preferred compounds according to the invention are compound N in the R,R-configuration (R,R—N), compound T in the R-configuration (R-T), compound AE in the R,trans-configuration (R,trans-AE) and compound X in any configuration, wherein $R^4=H$ and $X=Cl$, more preferably the compound according to the invention is compound X in the S,R-configuration (S,R—X), wherein $R^4=H$ and $X=Cl$. In one embodiment, these most preferred compounds according to the invention are compound N in the R,R-configuration (R,R—N), compound T in the R-configuration (R-T), compound AE in the R,trans-configuration (R,trans-AE) and compound X in any configuration, wherein $R^4$ and X are absent, most preferably the compound according to the invention is compound X in the S,R-configuration (S,R—X), wherein $R^4$ and X are absent.

The invention also includes all stereoisomers and geometric isomers of the compounds, including diastereomers, enantiomers, and cis/trans (E/Z) isomers. The invention also includes mixtures of stereoisomers and/or geometric isomers in any ratio, including, but not limited to, racemic mixtures.

In one embodiment, the compound according to the invention is not the compound represented by structure (I), wherein:

L=—C(iPr)-C(O)—NH—C(4-chlorobenzyl)-C(O)—C(O)—, $R^1=H$, $R^2=$—CH$_2$—CH$_3$ (Et), $R^3=H$, $R^4=X=$absent; and/or L=—(CH$_2$)$_2$—NR$^1$-pPh-N=C(thiophen-2-yl)-, $R^1$-$R^{1'}=$—(CH$_2$)$_2$-(L$^1$), $R^2=H$, $R^3=H$; $R^4=X=$absent, wherein pPh represents a para-substituted phenylene ring; and/or L=—(CH$_2$)$_2$-(L$^1$), $R^1=H$, $R^2=Me$, $R^3=Me$, $R^4=X=$absent; and/or L=—CH$_2$—C$_p$(R$^2$)—(C$_p$H)$_2$—, R$^1$=H, R$^2$-R$^2{'}$=—(C$_p$H)$_2$—, R$^3$=R$^4$=X=absent, wherein all instances of C$_p$ together with the distal nitrogen atom make up a pyridine ring; and/or L=—CH$_2$—C$_p$(R$^2$)—C$_p$H—, R$^1$=H, R$^2$-R$^2{'}$=—(C$_p$H)$_3$—, R$^3$=R$^4$=X=absent, wherein all instances of C$_p$ together with the distal nitrogen atom make up a pyridine ring; and/or L=—CH$_2$—C$_p$(R$^2$)—, R$^1$=H, R$^2$-R$^2{'}$=—(C$_p$H)$_4$—, R$^3$=R$^4$=X=absent, wherein all instances of C$_p$ together with the distal nitrogen atom make up a pyridine ring; and/or L=—(CH$_2$)$_3$-(L$^3$), R$^1$=H, R$^2$=Me, R$^3$=Me, R$^4$=X=absent; and/or L=—(CH$_2$)$_2$-(L$^1$), R$^1$-R$^2$=—(CH$_2$)$_2$-(L$^1$), R$^3$=Me, R$^4$=X=absent; and/or L=—(CH$_2$)$_2$-(L$^1$), R$^1$-R$^2$=—(CH$_2$)$_2$-(L$^1$), R$^3$=H, R$^4$=X=absent; and/or L=—(CH$_2$)$_2$—C$_p$(R$^2$)—, R$^1$=H, R$^2$-R$^2{'}$=—(C$_p$H)$_4$—, R$^3$=R$^4$=X=absent, wherein all instances of C$_p$ together with the distal nitrogen atom make up a pyridine ring; and/or L=—(CH$_2$)$_3$—N$_i$(R$^2$)—C$_i$H—, R$^1$=H, R$^2$-R$^2{'}$=—(C$_i$H)$_2$—, R$^3$=R$^4$=X=absent, wherein all instances of C$_i$ together with N$_i$ and the distal nitrogen atom make up an imidazole ring; and/or L=—(CH$_2$)$_2$-(L$^1$), R$^1$-R$^2$=—(CH$_2$)$_2$-(L$^1$), R$^3$=iPr, R$^4$=X=absent; and/or L=—C(R$^5$)=C(R$^5$)—, R$^1$=H, R$^2$=H, R$^3$=H, R$^4$=X=absent, R$^5$-R$^5$=—C(O)—N(Me)-C(O)—N(Ph)-, wherein linker R$^5$-R$^5$ is bound via the C(O) moiety to the carbon atom adjacent the amide nitrogen atom and via the N(Ph) moiety to the carbon atom adjacent the distal nitrogen atom; and/or L=—(CH$_2$)$_2$-(L$^1$), R$^1$=H, R$^2$=Me, R$^3$=Me, R$^4$=H; X=Cl; and/or L=—(CH$_2$)$_2$-(L$^1$), R$^1$=H, R$^2$=Me, R$^3$=Me, R$^4$=H; X=MeSO$_3$.

The compounds can be administered in prodrug form. Prodrugs are derivatives of the compounds which are themselves relatively inactive, but which convert into the active compound when introduced into the subject in which they are used, by a chemical or biological process in vivo, such as an enzymatic conversion. Suitable prodrug formulations include, but are not limited to peptide conjugates of the compounds of the invention and esters of compounds of the inventions. Further discussion of suitable prodrugs is provided in H. Bundgaard, Design of Prodrugs (New York: Elsevier, 1985); in R. Silverman, The Organic Chemistry of Drug Design and Drug Action (Boston: Elsevier, 2004); in R. L. Juliano, Biological Approaches to the Controlled Delivery of Drugs (Annals of the New York Academy of Sciences, volume 507, New York: N. Y. Academy of Sciences, 1987); and in E. B. Roche, Design of Biopharmaceutical Properties Through Prodrugs and Analogs (Symposium sponsored by Medicinal Chemistry Section, APhA Academy of Pharmaceutical Sciences, November 1976 national meeting, Orlando, Fla.), published by The Academy in Washington, 1977.

The various compounds of the invention can be administered either as therapeutic or cosmetic agents in and of themselves, or as prodrugs which will convert to other effective substances in the body. Preferably, the compounds according to the invention are administered as such, i.e. not as prodrug.

The compounds of the invention are useful for modulating ROS levels, as well as for modulating mitochondrial morphology, i.e. either mitochondrial fragmentation or mitochondrial filamentation, and/or for modulating the expression (i.e. steady-state levels) of OXPHOS enzymes, such as complex I and complex II. Thus, in one aspect, the invention relates to the use of the compounds of the invention in therapeutic and/or cosmetic methods for modulating at least one of mitochondrial morphology, expression of OXPHOS enzymes and ROS levels, preferably for modulating ROS levels.

In one embodiment, the effect of the compounds of the invention includes one or more of induction of mitochondrial filamentation, prevention or reduction of mitochondrial fragmentation, and increased expression of OXPHOS enzymes. Preferred compounds for this embodiment are compounds wherein the linkers are L$^5$, L$^8$, L$^{11}$, L$^{12}$, L$^{16}$, L$^{17}$, L$^{19}$, L$^{21}$ and L$^{26}$, preferably in these compounds the linkers are L, L$^{16}$, L$^{19}$ and L$^{26}$, and most preferred the linkers according to this embodiment of the invention is L$^{19}$. More specifically, preferred compounds of the invention having one or more of these effects are compounds F, K, N, O, U, V, T, X, Z, AE, AF, AG and AH. More preferred compounds according to the invention having one or more of these effects are compounds N T, X and AE. The most preferred compound according to this embodiment of the invention is compound X.

Compounds according to the invention can for example be prepared from compounds of general structure (II) by means known in the art.

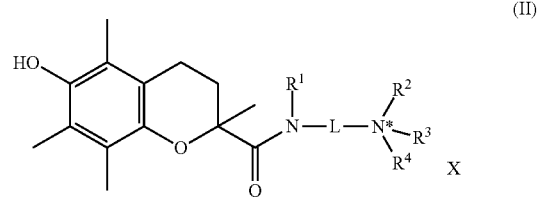

(II)

Herein, L, R$^1$, R$^2$, R$^3$, R$^4$ and X are as defined for the compounds of general structure (I). Compounds of general structure (II), and the synthesis thereof, are known from WO 2014/011047. The skilled person finds further guidance for preparing the compounds according to the invention in Example 1.

In another aspect, the invention relates to a compound of the invention as herein defined above for use as a medicament. The medicament can be used for both medical (human) as well as veterinary (animal) applications.

In a further aspect, the invention pertains to method of treating, preventing, or suppressing symptoms associated with a pathology, condition or disorder associated with an increased or an decreased ROS level, the method comprising administering to a subject an effective amount of one or more compounds of the invention as defined herein above. Alternatively, the invention relates to a compound as defined herein for use in treating, preventing or suppressing symptoms associated with a pathology, condition or disorder associated with an increased or an decreased ROS level. Preferably, the compound as defined herein can be used in treating, preventing or suppressing symptoms associated with a pathology, condition or disorder associated with an increased ROS level. The methods of the invention preferably comprise administering to a subject an effective amount of one or more compounds of the invention as herein defined above, and an acceptable carrier, excipient or vehicle, preferably a pharmaceutically or physiologically acceptable carrier, excipient or vehicle.

An increase in ROS levels causes oxidative stress, and the terms "increased ROS levels" and "oxidative stress" can be used interchangeable herein. An increased ROS level/oxidative stress is herein further defined as the imbalance between the systemic manifestation of reactive oxygen species and the system's ability to detoxify the intermediates, or to repair the resulting damage. ROS (reactive oxygen species) are chemically reactive molecules containing oxygen, such as e.g. hydroxyl radical (OH), hydrogen peroxide ($H_2O_2$), superoxide radical ($.O_2^-$). They are produced intracellularly through multiple mechanisms depending on the cell and tissue type. Alternatively, ROS can be generated by exogenous sources such as ionizing radiation. The major source of intracellular ROS comes from NAD (P)H oxidase complexes that are present in cell membranes, mitochondria, peroxisomes, and endoplasmic reticulum. For example, ROS are produced in the mitochondria as byproducts of normal cell respiration (Kirkinezos IG and Moraes C T, Semin Cell Dev Biol.; 12(6):449-457). Other sources of ROS include mitochondrial electron transport enzymes, xanthine oxidase, cyclooxygenase, lipoxygenase, and uncoupled nitric oxide synthase.

ROS play an important role in may physiological processes such as host defence, cell signalling, hormone biosynthesis, fertilization and homeostasis. However when intracellular ROS levels become too high, significant damage to cell structures may occur. The most common harmful effects of reactive oxygen species include DNA damage, oxidation of polyunsaturated fatty acids in lipids (lipid peroxidation), oxidation of amino acids in proteins and oxidatively deactivate specific enzymes by oxidation of co-factors.

Consequently, increased ROS levels have been linked to either the primary or secondary pathophysiologic mechanisms of acute and chronic human diseases, such as Sickle cell disease, Alzheimer disease, Spinal cord injury, Systemic lupus erythematosus, Asthma, Systemic sclerosis (scleroderma), Unstable angina, Cutaneous leishmaniasis, Zellweger syndrome, Preeclampsia, ARDS, Alcoholic liver disease, Atherosclerosis, Asbestosis, Ataxia telangiectasia, ALS, Cancer, Mild cognitive impairment, Diabetes mellitus (both types), HIV, Idiopathic pulmonary fibrosis, Acute and chronic alcoholic liver disease, Ischemic brain, Parkinson disease, Acute chest syndrome of sickle cell disease, Respiratory distress syndrome, Retinopathy of prematurity, Werner syndrome, Cardiopulmonary bypass, Cataract genesis, Chronic kidney disease, COPD, Friedreich ataxia, HIV infections, Creutzfeldt-Jakob disease, Hyperlipidemia, Renal cell carcinoma, Spherocytosis, Uremia associated with hemodialysis or peritoneal dialysis, Down syndrome, Heart failure, Hepatic cirrhosis, Huntington disease, Hypercholesterolemia, Hyperhomocysteinemia, Ischemia/Reperfusion injury, Interstitial lung disease, Myocardial infarction, Obesity, Crohn disease, Osteoporosis, Pancreatitis, Primary biliary cirrhosis, Psoriatic arthritis, Pulmonary hypertension, Lung injury, Reactive arthritis, Multiple sclerosis, Myocardial inflammation, Osteoarthritis, Rheumatoid arthritis, Severe bronchopulmonary dysplasia in neonates, Synucleinopathies, Tauopathies, Cardiovascular disease, Coronary artery disease, End-stage renal disease, Aceruloplasminemia, Acute autoimmune myocarditis, Acute pancreatitis, Bronchopulmonary dysplasia, Cataractogenesis, Chronic fatigue syndrome, Chronic hepatitis C, Chronic renal failure, Cystic fibrosis, Diabetes (types 1 and 2), *Helicobacter pylori* infection and inflammation, Juvenile chronic arthritis, Lung cancer, Meningitis, Progeria, Psoriasis, Sarcoidosis, Sepsis, Systemic amyloidosis, Uremia (Dalle-Donne et al, Clinical Chem. (2006), 52(4): 601-623).

In an embodiment of the invention, the compound as described herein can be used for the treatment, prevention or suppression of symptoms of any one of the diseases/conditions/pathologies listed herein above.

In a further preferred embodiment, the invention relates to a compound for use in treating, preventing, or suppressing symptoms associated with Parkinson Disease, Alzheimer Disease, Epilepsy, Dementia, Asthma, Amyotrophic Lateral Sclerosis, Inborn metabolism errors, Systemic sclerosis, Atherosclerosis, Osteoarthritis, Rheumatoid arthritis, Xenobiotics toxicity, Post-ischemic Reperfusion injury, Hypertension, Pulmonary hypertension, Pulmonary edema, Bowel disease, Endometriosis, Diabetes, Diabetes-induced cardiac dysfunction, Diabetic nephropathy, Cancer, Embryonal rhabdomyosarcoma, congenital muscular dystrophies, dystrophinopathies Adrenoleukodystrophy, a mitochondrial disorder and a condition associated with mitochondrial dysfunction.

In a further preferred embodiment, the inborn metabolism error is a lysosomal storage disorder, such as Gaucher's disease or Batten disease, and/or the inborn metabolism error is a disorder of peroxisomal function, such as Zellweger syndrome.

Reactive oxygen species is the general name for a number of reactive molecules and free radicals derived from oxygen. In particular, reactive oxygen species include superoxide, hydrogen peroxide, hydroxyl radical, hydroxyl ion and nitric oxide. Superoxide is the primary reactive oxygen species from which the others originate during detoxification by superoxide dismutase (SOD). The compounds of the invention may be particularly useful for decreasing the level of intracellular superoxide. The superoxide level may be decreased towards homeostatic levels and/or may be decreased below homeostatic levels. In particular, the superoxide levels in cell may be decreased even when there are no aberrant superoxide levels, e.g. the superoxide levels are not above homeostatic levels. Such decrease of super oxide may be particularly useful if a reactive oxygen species derived from super oxide detoxification is increased above homeostatic levels.

In a particular embodiment, the invention relates to a compound as defined herein for use in treating, preventing or suppressing symptoms associated with of a pathology, condition or disorder associated with an increased superoxide levels. Increased superoxide levels may originate from defects in enzymes that produce superoxide (e.g. NADPH oxidases) and/or enzymes involved in the detoxification of superoxides (e.g. SODs, catalases and/or peroxidases). A pathology, condition or disorder linked to defects in enzymes that produce superoxide include, but is not limited to, mitochondrial diseases (e.g. mitochondrial Complex I or III deficiency), hypertension, diabetes, atherosclerosis, cardiovascular disease and neurodegeneration (Paravicini™ et al, Diabetes Care 2008: S170-80). A pathology, condition or disorder linked to a dysfunction of enzymes responsible for the detoxification of superoxide includes, but is not limited to amyotrophic lateral sclerosis (ALS) (Muyderman H et al Br. J Pharmacol 2014; 171(8):2191-205).

In a particularly preferred embodiment, the invention relates to a compound as defined herein for use in treating, preventing or suppressing symptoms associated with an pathology, condition or disorder associated with an increased ROS level, wherein the disorder is a mitochondrial disorder and/or wherein the condition is a condition associated with mitochondrial dysfunction. In a further preferred embodiment, the mitochondrial disorder is a disorder selected from the group consisting of Myoclonic epilepsy; Myoclonic Epilepsy with Ragged Red Fibers (MERRF); Leber's Hereditary Optic Neuropathy (LHON); neuropathy ataxia and retinitis pigmentosa (NARP); Mitochondrial Myopathy, Encephalopathy, Lactacidosis, Stroke (MELAS); Leigh syndrome; Leigh-like syndrome; Dominant Optic atrophy (DOA); Kearns-Sayre Syndrome (KSS); Maternally Inherited Diabetes and Deafness (MIDD); Alpers-Huttenlocher syndrome; Ataxia Neuropathy spectrum; Chronic Progressive External Ophthalmoplegia (CPEO); Pearson syndrome; Mitochondrial Neuro-Gastro-Intestinal Encephalopathy (MNGIE); Sengers syndrome; 3-methylglutaconic aciduria, sensorineural deafness, encephalopathy and neuro-radiological findings of Leigh-like syndrome (MEGDEL); myopathy; mitochondrial myopathy; cardiomyopathy; encephalomyopathy, SURF1 (COX deficient Leigh syndrome due to complex IV surfeit protein deficiency) and isolated or combined OXPHOS deficiencies with so far unsolved genetic defect including disturbed pyruvate oxidation and ATP plus PCr production rates. In another preferred embodiment, the condition associated with mitochondrial dysfunction preferably is a condition selected from the group consisting of Friedreich's Ataxia (FRDA); renal tubular acidosis; Parkinson's disease; Alzheimer's disease; amyotrophic lateral sclerosis (ALS); Huntington's disease; developmental pervasive disorders; hearing loss; deafness; congenital muscular dystrophies, dystrophinopathies, diabetes; ageing; and adverse drug effects hampering mitochondrial function.

In a further aspect, the invention relates to a method of treating, preventing, or suppressing symptoms associated with a mitochondrial disorder or with a condition associated with mitochondrial dysfunction, the method comprising administering to a subject an effective amount of one or more compounds of the invention as herein defined above. Alternatively, the invention relates to a compound of the invention as herein defined above, for use in a method of treating, preventing, or suppressing symptoms associated with a mitochondrial disorder or with a condition associated with mitochondrial dysfunction. The methods of the invention preferably comprise administering to a subject an effective amount of one or more compounds of the invention as herein defined above, and an acceptable carrier, excipient or vehicle, preferably a pharmaceutically or physiologically acceptable carrier, excipient or vehicle.

Preferred compounds of the invention for treating a mitochondrial disorder and/or a condition associated with mitochondrial dysfunction are compounds of which the effect includes one or more of induction of mitochondrial filamentation, prevention or reduction of mitochondrial fragmentation, increased expression of OXPHOS enzymes, and decreased ROS levels, preferably decreased ROS levels, as defined herein above.

In the methods of the invention, the mitochondrial disorder and/or the condition associated with mitochondrial dysfunction preferably is a condition characterised by oxidative stress and/or a condition characterized by an OXPHOS deficiency. Every cell needs energy. Shortage of energy therefore affects the activity of every cell. Thus in principle every cell is affected by a sub-optimal amount of one or more of the OXPHOS complexes. However, the actual amount that is sub-optimal varies from cell to cell. Cells that have a relatively high energy consumption such as brain and muscle cells typically require a higher amount of OXPHOS system complexes than cells that have a low energy consumption, such as resting T-cells. Thus, the cells that are affected by said deficiency associated with an oxidative phosphorylation deficiency are typically, but not necessarily muscle cells or brain cells. Mitochondrial disorders are pleiotropic in their clinical manifestation. Various tissues can be affected like for instance pancreas, heart, liver, eye, inner ear, blood, colon and kidney. In addition, also cells from non-clinically affected tissues like fibroblasts often show a mitochondrial defect. Cells affected by an OXPHOS deficiency can be treated and provided with a higher amount of OXPHOS complex by providing the cell with a compound of the invention. A cell is affected by an OXPHOS deficiency when the OXPHOS capacity is lower than normal (i.e. a comparable cell of the same species from a healthy individual). The capacity is typically lower over a prolonged period of time. Apart from being derived from an individual with an OXPHOS deficiency there are several methods to determine whether a cell has an OXPHOS deficiency, such tests encompass but are not limited to oxygen consumption, ATP production capacity, and enzymatic activities of individual OXPHOS complexes (Chretien and Rustin J Inherit Metab Dis. 2003;_26_(2-3): 189-98). It has surprisingly been found that administration of a compound of the invention to a cell, results in higher amounts of OXPHOS complexes, (i.e. the mitochondria of the cells).

In the methods of the invention, the mitochondrial disorder preferably is a disorder selected from the group consisting of Myoclonic epilepsy; Myoclonic Epilepsy with Ragged Red Fibers (MERRF); Leber's Hereditary Optic Neuropathy (LHON); Neuropathy, Ataxia and Retinitis Pigmentosa (NARP); Mitochondrial Myopathy, Encephalopathy, Lactacidosis, Stroke (MELAS); Leigh syndrome; Leigh-like syndrome; Dominant Optic atrophy (DOA); Kearns-Sayre Syndrome (KSS); Maternally Inherited Diabetes and Deafness (MIDD); Alpers-Huttenlocher syndrome; Ataxia Neuropathy spectrum; Chronic Progressive External Ophthalmoplegia (CPEO); Pearson syndrome; Mitochondrial Neuro-Gastro-Intestinal Encephalopathy (MNGIE); Sengers syndrome; 3-methylglutaconic aciduria, sensorineural deafness, encephalopathy and neuro-radiological findings of Leigh-like syndrome (MEGDEL); SURF1 Leigh syndrome; myopathy; mitochondrial myopathy; cardiomyopathy; encephalomyopathy and isolated or combined oxidative phosphorylation disorders In the methods of the invention, the condition associated with mitochondrial dysfunction preferably is a condition selected from the group consisting of Friedreich's Ataxia (FRDA); renal tubular acidosis; Parkinson's disease; Alzheimer's disease; amyotrophic lateral sclerosis (ALS); Huntington's disease; Barth syndrome (also known as 3-Methylglutaconic aciduria type II); macula degeneration, preferably age-related macula degeneration; developmental pervasive disorders; hearing loss, deafness; congenital muscular dystrophies, dystrophinopathies, diabetes; ageing; adverse drug effects hampering (normal) mitochondrial function, including e.g. mitochondrial dysfunction caused by nucleoside analogue reverse transcriptase inhibitors (NRTIs), certain antibiotics and anti-epileptic drugs; and ischemia and reperfusion injury, preferably ischemic reperfusion injury after acute myocardial infarction (AMI), after stroke, including perinatal stroke, after haemorrhagic shock, after intestinal ischemia, after emergency coronary surgery for failed percutaneous transluminal coronary angioplasty (PCTA), after vascular surgery with blood vessel cross clamping (e.g. of aorta, leading to skeletal muscle ischemia), after pancreatitis after manipulation of pancreatic or bile duct (ERCP), and/or after organ transplantation.

In the methods of the invention, "subject", "individual", or "patient" is understood to be an individual organism, preferably a vertebrate, more preferably a mammal, most preferably a human.

"Treating" a disease with the compounds and methods discussed herein is defined as administering one or more of the compounds discussed herein, with or without additional therapeutic agents, in order to reduce or eliminate either the disease or one or more symptoms of the disease, or to retard the progression of the disease or of one or more symptoms of the disease, or to reduce the severity of the disease or of one or more symptoms of the disease. "Suppression" of a disease with the compounds and methods discussed herein is defined as administering one or more of the compounds discussed herein, with or without additional therapeutic agents, in order to suppress the clinical manifestation of the disease, or to suppress the manifestation of adverse symptoms of the disease. The distinction between treatment and suppression is that treatment occurs after adverse symptoms of the disease are manifest in a subject, while suppression occurs before adverse symptoms of the disease are manifest in a subject. Suppression may be partial, substantially total, or total. Because many of the mitochondrial disorders are inherited, genetic screening can be used to identify patients at risk of the disease. The compounds and methods of the invention can then be administered to asymptomatic patients at risk of developing the clinical symptoms of the disease, in order to suppress the appearance of any adverse symptoms. "Therapeutic use" of the compounds discussed herein is defined as using one or more of the compounds discussed herein to treat or suppress a disease, as defined above. An "effective amount" of a compound is an amount of a compound which, when administered to a subject, is sufficient to reduce or eliminate either one or more symptoms of a disease, or to retard the progression of one or more symptoms of a disease, or to reduce the severity of one or more symptoms of a disease, or to suppress the manifestation of a disease, or to suppress the manifestation of adverse symptoms of a disease. An effective amount can be given in one or more administrations.

Several readily measurable clinical markers are used to assess the metabolic state of patients with mitochondrial disorders. These markers can also be used as indicators of the efficacy of the therapy using the compounds of the invention, as the level of a marker is moved from the pathological value to the healthy value. These clinical markers include, but are not limited to, one or more of the energy biomarkers, such as lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; amino acids, in particular alanine, citrulline and proline either in whole blood, plasma, cerebrospinal fluid, organic acids in body fluids, FGF21 in serum and skeletal muscle, phosphocreatine levels, NADH (NADH+H$^+$) or NADPH (NADPH+H$^+$) levels; NAD or NADP levels; ATP levels; anaerobic threshold; reduced coenzyme Q (CoQ$^{red}$) levels; oxidized coenzyme Q (CoQ$^{ox}$ levels; total coenzyme Q (CoQ$^{tot}$) levels; oxidized cytochrome C levels; reduced cytochrome C levels; oxidized cytochrome C/reduced cytochrome C ratio; acetoacetate levels, beta-hydroxy butyrate levels, acetoacetate/betahydroxy butyrate ratio, 8-hydroxy-2'-deoxyguanosine (8-OHdG) levels; levels of reactive oxygen species; and levels of oxygen consumption (VO2), levels of carbon dioxide output (VCO2), and respiratory quotient (VCO2/VO2).

Additional biomarkers that can be used as indicators of the efficacy of the therapy using the compounds of the invention include MDA, HNE, Acrolein, F$_2$—Isoprostanes, a decrease in GSH concentration and/or GSH/GSSG ratio, S-Glutathionylated proteins, 3-nitrotyrosine (NO$_2$-Tyr), 3-chlorotyrosine (Cl-Tyr), o,o'-dityrosine (Di-Tyr), and Carbonylated proteins (Dalle-Donne et al, Clinical Chem. (2006), 52(4): 601-623).

These biomarkers are particularly useful for measuring a decrease in ROS levels (oxidative stress) after treatment with a compound of the invention. In an embodiment of the invention, the level of one or more of these biomarkers in a patient suffering from a disease that is associated with an increased oxidative stress is improved to within two standard deviations of the average level in a healthy subject. Diseases associated with an increased oxidative stress are outlined above, and including, but not limited to, Parkinson Disease, Alzheimer Disease, Epilepsy, Dementia, Asthma, Amyotrophic Lateral Sclerosis, Inborn metabolism errors, Systemic sclerosis, Atherosclerosis, Osteoarthritis, Rheumatoid arthritis, Xenobiotics toxicity, Post-ischemic Reperfusion injury, Hypertension, Pulmonary hypertension, Pulmonary edema, Bowel disease, Endometriosis, Diabetes, Diabetes-induced cardiac dysfunction, Diabetic nephropathy, Cancer, Embryonal rhabdomyosarcoma and Adrenoleukodystrophy.

Several of these clinical markers are measured routinely in exercise physiology laboratories, and provide convenient assessments of the metabolic state of a subject. In one embodiment of the invention, the level of one or more energy biomarkers in a patient suffering from a mitochondrial disease, such as Friedreich's ataxia, Leber's hereditary optic neuropathy, dominant optic atrophy, Leigh syndrome, SURF1, MERRF, MELAS, or KSS, is improved to within two standard deviations of the average level in a healthy subject after administration of an effective amount of a compound of the invention. In another embodiment of the invention, the level of one or more of these energy biomarkers in a patient suffering from a mitochondrial disease, such as Friedreich's ataxia, Leber's hereditary optic neuropathy, dominant optic atrophy, Leigh syndrome, SURF1, MERRF, MELAS, or KSS is improved to within one standard deviation of the average level in a healthy subject after administration of an effective amount of a compound of the invention. Exercise intolerance can also be used as an indicator of the efficacy of a given therapy, where an improvement in exercise tolerance (i.e. a decrease in exercise intolerance) indicates efficacy of a given therapy.

Several metabolic biomarkers have already been used to evaluate efficacy of CoQ$_{10}$, and these metabolic biomarkers can be monitored as energy biomarkers for use in the methods of the current invention. Pyruvate, a product of the anaerobic metabolism of glucose, is removed by reduction to lactic acid in an anaerobic setting or by oxidative metabolism, which is dependent on a functional mitochondrial OXPHOS. Dysfunction of the OXPHOS may lead to inadequate removal of lactate and pyruvate from the circulation and elevated lactate/pyruvate ratios are observed in mitochondrial cytopathies (see Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)). Blood lactate/pyruvate ratio (Chariot et al., Arch. Pathol. Lab. Med. 118(7):695-7 (1994)) is, therefore, widely used as a noninvasive test for detection of mitochondrial cytopathies (see again Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)) and toxic mitochondrial myopathies (Chariot et al., Arthritis Rheum. 37(4): 583-6 (1994)). Changes in the redox state of liver mitochondria can be investigated by measuring the arterial ketone body ratio (acetoacetate/3-hydroxybutyrate:AKBR) (Ueda et al., J. Cardiol. 29(2):95-102 (1997)). Urinary excretion of 8-hydroxy-2'-deoxyguanosine (8-OHdG) often has been used as a biomarker to assess the extent of repair of ROS-induced DNA damage in both clinical and occupational settings (Erhola et al., FEBS Lett. 409(2):287-91 (1997); Honda et al., Leuk. Res. 24(6):461-8 (2000); Pilger et al., Free Radic. Res. 35(3):273-80 (2000); Kim et al., Environ Health Perspect 112(6):666-71(2004)).

Magnetic resonance spectroscopy (MRS) has been useful in the diagnoses of mitochondrial cytopathy by demonstrating elevations in cerebrospinal fluid (CSF) and cortical white matter lactate using proton MRS (H-MRS) (Kaufmann et al., Neurology 62(8):1297-302 (2004)). Phosphorous MRS ($^{31}$P-MRS) has been used to demonstrate low levels of cortical phosphocreatine (PCr) (Matthews et al., Ann. Neurol. 29(4):435-8 (1991)), and a delay in PCr recovery kinetics following exercise in skeletal muscle (Matthews et al., Ann. Neurol. 29(4):435-8 (1991); Barbiroli et al., J. Neurol. 242(7):472-7 (1995); Fabrizi et al., J. Neurol. Sci. 137(1):20-7 (1996)). A low skeletal muscle PCr has also been confirmed in patients with mitochondrial cytopathy by direct biochemical measurements.

Exercise testing is particularly helpful as an evaluation and screening tool in mitochondrial myopathies, and an improvement in exercise tolerance indicates the efficacy of a given therapy with a compound of the invention. One of the hallmark characteristics of mitochondrial myopathies is a reduction in maximal whole body oxygen consumption (VO2max) (Taivassalo et al., Brain 126(Pt 2):413-23 (2003)). Given that VO2max is determined by cardiac output (Qc) and peripheral oxygen extraction (arterial-venous total oxygen content) difference, some mitochondrial cytopathies affect cardiac function where delivery can be altered; however, most mitochondrial myopathies show a characteristic deficit in peripheral oxygen extraction (A-V 02 difference) and an enhanced oxygen delivery (hyperkinetic circulation) (Taivassalo et al., Brain 126(Pt 2):413-23 (2003)). This can be demonstrated by a lack of exercise induced deoxygenation of venous blood with direct AV balance measurements (Taivassalo et al., Ann. Neurol. 51(1):38-44 (2002)) and non-invasively by near infrared spectroscopy (Lynch et al., Muscle Nerve 25(5):664-73 (2002); van Beekvelt et al., Ann. Neurol. 46(4):667-70 (1999)).

Several of these energy biomarkers are discussed in more detail as follows. It should be emphasized that, while certain energy biomarkers are discussed and enumerated herein, the invention is not limited to modulation, normalization or enhancement of only these enumerated energy biomarkers.

Lactic acid (lactate) levels: Mitochondrial dysfunction typically results in abnormal levels of lactic acid, as pyruvate levels increase and pyruvate is converted to lactate to maintain capacity for glycolysis. Mitochondrial dysfunction can also result in abnormal levels of NADH+H$^+$, NADPH+ H$^+$, NAD, or NADP, as the reduced nicotinamide adenine dinucleotides are not efficiently processed by the respiratory chain. Lactate levels can be measured by taking samples of appropriate bodily fluids such as whole blood, plasma, or cerebrospinal fluid. Using magnetic resonance, lactate levels can be measured in virtually any volume of the body desired, such as the brain.

Measurement of cerebral lactic acidosis using magnetic resonance in MELAS patients is described in Kaufmann et al., Neurology 62(8):1297 (2004). Values of the levels of lactic acid in the lateral ventricles of the brain are presented for two mutations resulting in MELAS, mt.3243A>G and mt.8344A>G. Whole blood, plasma, and cerebrospinal fluid lactate levels can be measured by commercially available equipment such as the YSI 2300 STAT Plus Glucose & Lactate Analyzer (YSI Life Sciences, Ohio).

NAD, NADP, NADH and NADPH levels: Measurement of NAD, NADP, NADH (NADH+H$^+$) or NADPH (NADPH+H$^+$) can be measured by a variety of fluorescent, enzymatic, or electrochemical techniques, e. g., the electrochemical assay described in US2005/0067303.

Oxygen consumption (vO$_2$ or VO2), carbon dioxide output (vCO$_2$ or VCO2), and respiratory quotient (VCO2/VO2): vO$_2$ is usually measured either while resting (resting vO$_2$) or at maximal exercise intensity (vO$_2$ max). Optimally, both values will be measured. However, for severely disabled patients, measurement of vO$_2$ max may be impractical. Measurement of both forms of vO$_2$ is readily accomplished using standard equipment from a variety of vendors, e.g. Korr Medical Technologies, Inc. (Salt Lake City, Utah). VCO2 can also be readily measured, and the ratio of VCO2 to VO2 under the same conditions (VCO2/VO2, either resting or at maximal exercise intensity) provides the respiratory quotient (RQ).

Oxidized Cytochrome C, reduced Cytochrome C, and ratio of oxidized Cytochrome C to reduced Cytochrome C: Cytochrome C parameters, such as oxidized cytochrome C levels (Cyt $C_{ox}$), reduced cytochrome C levels (Cyt $C^{red}$), and the ratio of oxidized cytochrome C/reduced cytochrome C ratio (Cyt $C^{ox}$)/(Cyt $C^{red}$), can be measured by in vivo near infrared spectroscopy. See, e. g., Rolfe, P., "In vivo near-infrared spectroscopy," Annu. Rev. Biomed. Eng. 2:715-54 (2000) and Strangman et al., "Non-invasive neuroimaging using near-infrared light" Biol. Psychiatry 52:679-93 (2002).

Exercise tolerance/Exercise intolerance: Exercise intolerance is defined as "the reduced ability to perform activities that involve dynamic movement of large skeletal muscles because of symptoms of dyspnea or fatigue" (Pina et al., Circulation 107:1210 (2003)). Exercise intolerance is often accompanied by myoglobinuria, due to breakdown of muscle tissue and subsequent excretion of muscle myoglobin in the urine. Various measures of exercise intolerance can be used, such as time spent walking or running on a treadmill before exhaustion, time spent on an exercise bicycle (stationary bicycle) before exhaustion, and the like. Treatment with the compounds or methods of the invention can result in about a 10% or greater improvement in exercise tolerance (for example, about a 10% or greater increase in time to exhaustion, e. g. from 10 minutes to 11 minutes), about a 20% or greater improvement in exercise tolerance, about a 30% or greater improvement in exercise tolerance, about a 40% or greater improvement in exercise tolerance, about a 50% or greater improvement in exercise tolerance, about a 75% or greater improvement in exercise tolerance, or about a 100% or greater improvement in exercise tolerance. While exercise tolerance is not, strictly speaking, an energy biomarker, for the purposes of the invention, modulation, normalization, or enhancement of energy biomarkers includes modulation, normalization, or enhancement of exercise tolerance.

Similarly, tests for normal and abnormal values of pyruvic acid (pyruvate) levels, lactate/pyruvate ratio, ATP levels, anaerobic threshold, reduced coenzyme Q ($CoQ^{red}$) levels, oxidized coenzyme Q ($CoQ^{ox}$) levels, total coenzyme Q ($CoQ^{tot}$) levels, oxidized cytochrome C levels, reduced cytochrome C levels, oxidized cytochrome C/reduced cytochrome C ratio, acetoacetate levels, beta-hydroxy butyrate levels, acetoacetate/beta-hydroxy butyrate ratio, 8-hydroxy-2'-deoxyguanosine (8-OHdG) levels, and levels of reactive oxygen species are known in the art and can be used to evaluate efficacy of the compounds and methods of the invention. (For the purposes of the invention, modulation, normalization, or enhancement of energy biomarkers includes modulation, normalization, or enhancement of anaerobic threshold).

Table 1, following, illustrates the effect that various dysfunctions can have on biochemistry and energy biomarkers. It also indicates the physical effect (such as a disease symptom or other effect of the dysfunction) typically associated with a given dysfunction. It should be noted that any of the energy biomarkers listed in the table, in addition to energy biomarkers enumerated elsewhere, can also be modulated, enhanced, or normalized by the compounds and methods of the invention. RQ=respiratory quotient; BMR=basal metabolic rate; HR (CO)=heart rate (cardiac output); T=body temperature (preferably measured as core temperature); AT=anaerobic threshold; pH=blood pH (venous and/or arterial).

TABLE 1

| Site of dysfunction | Biochemical event | Measurable Energy Biomarker | Physical Effect |
|---|---|---|---|
| OXPHOS | ↑ NADH | Δ lactate, Δ lactate:pyruvate ratio, Δ acetoacetate:β-hydroxybutyrate ratio | Metabolic dyscrasia & fatigue |
| OXPHOS | ↑ NADH | Amino acid | Metabolic dyscrasia & fatigue |
| OXPHOS | ↑ NADH | Organic acids | Metabolic dyscrasia & fatigue |
| OXPHOS | ↑ NADH | FGF21 | Metabolic dyscrasia & fatigue |
| OXPHOS | ↓ $H^+$ gradient | Δ ATP | Organ dependent dysfunction |
| OXPHOS | ↓ Electron flux | Δ $VO_2$, RQ, BMR, ΔT, AT, pH | Metabolic dyscrasia & fatigue |
| Mitochondria & cytosol | ↓ ATP, ↓ $VO_2$ | Δ Work, ΔHR (CO) | Exercise intolerance |
| Mitochondria & cytosol | ↓ ATP | Δ PCr | Exercise intolerance |
| Respiratory Chain | ↓ Cyt $C^{Ox/Red}$ | Δ ~ 700-900 nm (NIR spectroscopy) | Exercise intolerance |
| Intermediary metabolism | ↓ Catabolism | Δ $C^{14}$-labeled substrates | Metabolic dyscrasia & fatigue |
| Respiratory Chain | ↓ Electron flux | Δ Mixed venous $VO_2$ | Metabolic dyscrasia & fatigue |
| Mitochondria & cytosol | ↑ Oxidative stress | Δ Tocopherol & Tocotrienols, CoQ10 docosahexanoic acid | Uncertain |

TABLE 1-continued

| Site of dysfunction | Biochemical event | Measurable Energy Biomarker | Physical Effect |
|---|---|---|---|
| Mitochondria & cytosol | ↑ Oxidative stress | Δ $Glutathione^{red}$ | Uncertain |
| Mitochondria & cytosol | Nucleic acid oxidation | Δ 8-hydroxy 2-deoxy guanosine | Uncertain |
| Mitochondria & cytosol | Lipid oxidation | Δ Isoprostane(s), eicasanoids | Uncertain |
| Cell membranes | Lipid oxidation | Δ Ethane (breath) | Uncertain |
| Cell membranes | Lipid oxidation | Δ Malondialdehyde | Uncertain |

Treatment of a subject afflicted by a mitochondrial disease in accordance with the methods of the invention may result in the inducement of a reduction or alleviation of symptoms in the subject, e.g. to halt the further progression of the disorder.

Partial or complete suppression of the mitochondrial disease can result in a lessening of the severity of one or more of the symptoms that the subject would otherwise experience. For example, partial suppression of MELAS could result in reduction in the number of stroke-like or seizure episodes suffered.

Any one energy biomarker or any combination of the energy biomarkers described herein provides conveniently measurable benchmarks by which to gauge the effectiveness of treatment or suppressive therapy. Additionally, other energy biomarkers are known to those skilled in the art and can be monitored to evaluate the efficacy of treatment or suppressive therapy.

In a preferred embodiment, the efficacy of treatment or suppressive therapy with the methods of the inventions can be determined using one or more of the outcome measures of the toolbox as listed in Table 1 of Koene et al (2013, Dev. Med. Child Neurol. 55(8): 698-706), more preferably the efficacy is determined using one or more of the outcome measures of the "Common core set" in Table 1 of Koene et al (2013, supra).

The methods of the invention preferably comprise administering to a subject an effective amount of one or more compounds of the invention as herein defined above, and an acceptable carrier, excipient or vehicle, preferably a pharmaceutically or physiologically acceptable carrier, excipient or vehicle.

In yet another aspect the invention relates to the cosmetic use of the compounds of the invention. The compounds of the invention may thus be used (in methods) to revive the skin of a treated individual, particularly in individuals with aged skin, either due to aging or due to excessive exposure to sun. Both conditions are related to the production of free radicals in skin, such as ROS. By at least one of induction of mitochondrial filamentation, prevention or reduction of mitochondrial fragmentation, increased expression of OXPHOS enzymes and decreased ROS levels (e.g. superoxide levels) in a cell of said individual it is possible to lower the action of free radicals in the skin and at least delay further aging in the skin. As such, one can also use a composition of the invention as a prophylactic, i.e. to at least reduce free radicals that would be capable to act on the skin, if left untreated. Thus preferably in this aspect of the invention compounds of the invention are applied the effect of which includes one or more of induction of mitochondrial filamentation, prevention or reduction of mitochondrial fragmentation, increased expression of OXPHOS enzymes and decreased ROS levels, preferably decreased ROS levels. Preferred compounds having these effects are indicated herein above.

In a further aspect, the invention relates to a compound as disclosed herein for use as a conservative agent, preferably as a conservative agent in food. It is well-known in the art that antioxidants may help prevent the oxidation of feeds, especially fats and oils, and protect cells from free-radical damage. Therefore, food manufacturers use antioxidants as food additives to help guard against food degradation and enhance the health profile of functional foods. A compound of the invention may function as such antioxidant and hence act as food preservative.

The compounds of the invention can also be used in research applications, such as in vitro, in vivo, or ex vivo experiments in order to modulate one or more energy biomarkers in an experimental system. Such experimental systems can be cell samples, tissue samples, cell components or mixtures of cell components, partial organs, whole organs, or organisms. Such research applications can include, but are not limited to, use as assay reagents, elucidation of biochemical pathways, or evaluation of the effects of other agents on the metabolic state of the experimental system in the presence/absence of one or more compounds of the invention.

Additionally, the compounds of the invention can be used in biochemical tests or assays. Such tests can include incubation of one or more compounds of the invention with a tissue or cell sample from a subject to evaluate a subject's potential response (or the response of a specific subset of subjects) to administration of said one or more compounds, or to determine which compound of the invention produces the optimum effect in a specific subject or subset of subjects. One such test or assay would involve 1) obtaining a cell sample or tissue sample from a subject or set of subjects in which modulation of one or more energy biomarkers can be assayed; 2) administering one or more compounds of the invention to the cell sample(s) or tissue sample(s); and 3) determining the amount of modulation of the one or more energy biomarkers after administration of the one or more compounds, compared to the status of the energy biomarker prior to administration of the one or more compounds.

Another such test or assay would involve 1) obtaining a cell sample or tissue sample from a subject or set of subjects in which modulation of one or more energy biomarkers can be assayed; 2) administering at least two compounds of the invention to the cell sample(s) or tissue sample(s); 3) determining the amount of modulation of the one or more energy biomarkers after administration of the at least two compounds, compared to the status of the energy biomarker prior to administration of the at least two compounds, and 4) selecting a compound for use in treatment, suppression, or modulation based on the amount of modulation determined in step 3).

The compounds as described herein are able to scavenge cellular reactive oxygen species, such as superoxide. The compounds therefore may be used in ex vivo techniques that cause an (unwanted) increase in cellular reactive oxygen species. In a further aspect, the invention therefore pertains to an ex vivo method for scavenging oxygen species in a cell, wherein the method comprises a step of exposing the cell to the compound as defined herein.

The cell for use in a method of the invention may be any cell that can be used in an ex vivo technique. The cell may be a prokaryotic cell or an eukaryotic cell.

In a preferred embodiment, the cell is a eukaryotic cell such as a mammalian, insect, plant, fungal, yeast or algal cell. More preferably, the cell is a mammalian cell, such as e.g. a bovine, caprine, equine, ovine, porcine or primate cell, most preferably the cell is a human cell.

A preferred cell for use in the method of the invention is a somatic cell, a gamete, a gametocyte or an undifferentiated stem cell. More preferably, the cell is a somatic cell, and most preferably the somatic cell is a mammalian somatic cell.

The compounds of the invention scavenge cellular reactive oxygen species such as superoxide and can therefore be used in ex vivo techniques to counteract any unwanted increase in oxidative stress. Such unwanted increase in reactive oxygen species occurs for example during the reprogramming of somatic cells into pluripotent stem cells (induced pluripotent stem cells, iPSCs). iPSCs can subsequently be differentiated to other cell types in vitro. Alternatively, transdifferentiation yields the desired cell type without passing through a pluripotent stage. Both techniques require the presence of specific transcription factors to override the current transcriptional status and launches transcriptional activity characteristic of another, unrelated lineage (Novak et al, J Dtsch Dermatol Ges, (2014) 12(9):789-92).

Ji et al. (supra) teach increased levels of ROS and oxidative DNA damage during the early stages of reprogramming using the transcription factors OCT4, SOX2, KLF4 and c-MYC. In particular, the addition of antioxidants (such as Vitamin C and N-acetyl-cysteine) reduced both ROS and genomic double-strand breaks. Furthermore, a significant reduction in copy number variation (CNVs) was observed in the generated iPSCs after the addition of antioxidants. Thus supporting the redox balance may protect the somatic genome, leading to iPSCs with fewer genomic alterations.

In a preferred embodiment the method of the invention therefore pertains to an ex vivo method for scavenging reactive oxygen species in a cell wherein the method comprises a step of exposing a somatic cell to a compound as defined herein and wherein the somatic cell is further reprogrammed to an induced pluripotent stem cell (iPSC) by exposing the cell to at least one reprogramming factor.

The somatic cell may be any somatic cell suitable for the reprogramming the cell into iPSC or suitable for transdifferentiating the cell into another cell lineage. A preferred somatic cell for use in the method of the invention is a fibroblast, neuronal (progenitor) cell, hepatocyte, B cell, kidney cell, muscle cell, adrenal gland cell, keratinocyte, melanocyte, epithelial cell or a peripheral blood derived cell, preferably wherein the peripheral blood derived cell is an endothelial progenitor cell (L-EPCs) or a cord blood derived cell type (CD34+) (Yee, J. (2010). Nature Education 3(9): 25). Preferably, the somatic cell is an (embryonic) fibroblast or a peripheral blood derived cell.

Alternatively, the method of the invention relates to the use of a compound as disclosed herein for producing pluripotent stem cells, wherein the method comprises the steps of exposing a somatic cell to at least one reprogramming factor, and exposing the somatic cell to an effective amount of the compound of the invention.

The programming factor for use in the method of the invention may be any factor that induces the reprogramming of the somatic cell into an iPSC or differentiates the somatic cell into another cell lineage by transdifferentiation. Preferably, the reprogramming factor is at least one of Oct4, Sox2, KLF4, c-Myc, Lin28, Nanog, Glis1, Sall4, Esrrb and Nr5a2.

The reprogramming of the somatic cell may require the addition of at least 1, 2, 3, 4 or 5 reprogramming factors.

These reprogramming factors may be added sequentially or simultaneously to the somatic cell (Liu et al, Nature Cell Biol (2013) 15(7):829-38). Particularly preferred compositions of reprogramming factors are Oct4, Sox2, KLF4 and c-MYC (the Yamanaka factors), Oct4, Sox2, Nanog and Lin28 (the Thomson factors) or Sall4, Nanog, Esrrb and Lin28 (Buganim et al, Cell Stem Cell. (2014) 15(3): 295-309).

The compositions comprising the compounds of the invention, as described above, can be prepared as a medicinal or cosmetic preparation or in various other media, such as foods for humans or animals, including medical foods and dietary supplements. A "medical food" is a product that is intended for the specific dietary management of a disease or condition for which distinctive nutritional requirements exist. By way of example, but not limitation, medical foods may include vitamin and mineral formulations fed through a feeding tube (referred to as enteral administration). A "dietary supplement" shall mean a product that is intended to supplement the human diet and is typically provided in the form of a pill, capsule, and tablet or like formulation. By way of example, but not limitation, a dietary supplement may include one or more of the following ingredients: vitamins, minerals, herbs, botanicals; amino acids, dietary substances intended to supplement the diet by increasing total dietary intake, and concentrates, metabolites, constituents, extracts or combinations of any of the foregoing. Dietary supplements may also be incorporated into food, including, but not limited to, food bars, beverages, powders, cereals, cooked foods, food additives and candies; or other functional foods designed to promote cerebral health or to prevent or halt the progression of a neurodegenerative disease involving mitochondrial dysfunction. If administered as a medicinal preparation, the composition can be administered, either as a prophylaxis or treatment, to a patient in any of a number of methods. The compositions may be administered alone or in combination with other pharmaceutical or cosmetic agents and can be combined with a physiologically acceptable carrier thereof. The effective amount and method of administration of the particular formulation can vary based on the individual subject, the condition or the stage of disease, and other factors evident to one skilled in the art. During the course of the treatment, the concentration of the subject compositions may be monitored to insure that the desired level is maintained. The subject compositions may be compounded with other physiologically acceptable materials which can be ingested including, but not limited to, foods.

The inventions thus also pertains to pharmaceutical or cosmetic compositions comprising one or more compounds according to the invention. The compounds described herein can be formulated as pharmaceutical or cosmetic compositions by formulation with additives such as pharmaceutically or physiologically acceptable excipients carriers, and vehicles. Suitable pharmaceutically or physiologically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-P-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21" edition (2005), incorporated herein by reference.

A pharmaceutical or cosmetic composition can comprise a unit dose formulation, where the unit dose is a dose sufficient to have a therapeutic or suppressive effect or an amount effective to modulate, normalize, or enhance an energy biomarker. The unit dose may be sufficient as a single dose to have a therapeutic or suppressive effect or an amount effective to modulate, normalize, or enhance an energy biomarker. Alternatively, the unit dose may be a dose administered periodically in a course of treatment or suppression of a disorder, or to modulate, normalize, or enhance an energy biomarker.

Pharmaceutical or cosmetic compositions containing the compounds of the invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Time-release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the invention may be administered enterally, orally, parenterally, sublingually, by inhalation (e.g. as mists or sprays), rectally, or topically in dosage unit formulations containing conventional nontoxic pharmaceutically or physiologically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The compounds are mixed with pharmaceutically acceptable carriers, adjuvants, and vehicles appropriate for the desired route of administration. Oral administration is a preferred route of administration, and formulations suitable for oral administration are preferred formulations. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form that is therapeutically effective. Additional methods of administration are known in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at room temperature but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavouring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidylcholines (lecithins), both natural and synthetic. Methods to form liposomes are known in the art. See, for example, Prescott, Ed., Methods in Cell Biology, Volume XIV, Academic Press, New York, N.Y., p. 33 et seq (1976).

The invention also provides articles of manufacture and kits containing materials useful for treating, preventing, or suppressing symptoms associated with a mitochondrial disorder or with a condition associated with mitochondrial dysfunction. The article of manufacture comprises a container with a label. Suitable containers include, for example, bottles, vials, and test tubes. The containers may be formed from a variety of materials such as glass or plastic. The container holds a composition having an active agent that is effective for treating, preventing, or suppressing symptoms associated with a mitochondrial disorder or with a condition associated with mitochondrial dysfunction. The active agent in the composition is one or more of the compounds of the invention. The label on the container preferably indicates that the composition is used for treating, preventing, or suppressing symptoms associated with a mitochondrial disorder or with a condition associated with mitochondrial dysfunction, and may also indicate directions for either in vivo or in vitro use, such as those described above.

The invention also provides kits comprising any one or more of the compounds of the invention. In some embodiments, the kit of the invention comprises the container described above. In other embodiments, the kit of the invention comprises the container described above and a second container comprising a buffer. It may further include other materials desirable from a commercial and user standpoint, including other buffers, diluents, filters, needles, syringes, and package inserts with instructions for performing any methods described herein.

In other aspects, the kits may be used for any of the methods described herein, including, for example, methods for treating, preventing, or suppressing symptoms associated with a mitochondrial disorder or with a condition associated with mitochondrial dysfunction.

The amount of active ingredient that may be combined with the carrier materials to produce a single dosage form will vary depending upon the host to which the active ingredient is administered and the particular mode of administration. It will be understood, however, that the specific dose level for any particular patient will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy or condition to be treated. The unit dosage chosen is usually fabricated and administered to provide a defined final concentration of drug in the blood, tissues, organs, or other targeted region of the body. The effective amount for a given situation can be readily determined by routine experimentation and is within the skill and judgment of the ordinary clinician or skilled person.

Examples of dosages which can be used are an effective amount of the compounds of the invention within the dosage range of about 0.1 g/kg to about 300 mg/kg, or within about 1.0 g/kg to about 40 mg/kg body weight, or within about 1.0 g/kg to about 20 mg/kg body weight, or within about 1.0 g/kg to about 10 mg/kg body weight, or within about 10.0 g/kg to about 10 mg/kg body weight, or within about 100 µg/kg to about 10 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Other dosages which can be used are about 0.01 mg/kg body weight, about 0.1 mg/kg body weight, about 1 mg/kg body weight, about 10 mg/kg body weight, about 20 mg/kg body weight, about 30 mg/kg body weight, about 40 mg/kg body weight, about 50 mg/kg body weight, about 75 mg/kg body weight, about 100 mg/kg body weight, about 125 mg/kg body weight, about 150 mg/kg body weight, about 175 mg/kg body weight, about 200 mg/kg body weight, about 225 mg/kg body weight, about 250 mg/kg body weight, about 275 mg/kg body weight, or about 300 mg/kg body weight. Compounds of the present invention may be administered in a single daily dose, or the total daily dosage may be administered in divided dosage of two, three or four times daily.

While the compounds of the invention can be administered as the sole active pharmaceutical or cosmetic agent, they can also be used in combination with one or more other agents used in the treatment or suppression of disorders. Representative agents useful in combination with the compounds of the invention for the treating, preventing, or suppressing symptoms associated with a mitochondrial disorder or with a condition associated with mitochondrial dysfunction include, but are not limited to, Coenzyme Q, vitamin E, idebenone, MitoQ, Szeto-Schiller peptides, EPI-743, vitamin K and analogues thereof, naphtoquinones and derivatives thereof, other vitamins, and antioxidant compounds.

When additional active agents are used in combination with the compounds of the present invention, the additional active agents may generally be employed in therapeutic amounts as indicated in the Physicians' Desk Reference (PDR) 53rd Edition (1999), which is incorporated herein by reference, or such therapeutically useful amounts as would be known to one of ordinary skill in the art. The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the elements is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

DESCRIPTION OF THE FIGURES

FIG. 2A S,R—$X^{II}$ ($R^4$=H, X=Cl) and S,R—X ($R^4$=H, X=formate) in addition to the known compounds EPI743 and Idebenone, FIG. 2B Trolox and open Trolox, FIG. 2C R-$T^{II}$ ($R^4$=H, X=Cl) and R-T ($R^4$=H, X=formate), FIG. 2D R,R—$N^{II}$ ($R^4$=H, X=Cl) and R,R—N($R^4$=H, X=formate), FIG. 2E S,R—$N^{II}$ ($R^4$=H, X=Cl) and S,R—N($R^4$=H, X=formate), FIG. 2F R,R—$X^{II}$ ($R^4$=H, X=Cl) and R,R—X ($R^4$=H, X=formate), FIG. 2G R,S—$X^{II}$ ($R^4$=H, X=Cl) and R,S—X ($R^4$=H, X=formate) and FIG. 2H R,trans-$AE^{II}$ ($R^4$=H, X=Cl) and R,trans-AE ($R^4$=H, X=formate).

FIG. 4A S,R—$X^{II}$ ($R^4$=H, X=Cl) and S,R—X ($R^4$=H, X=formate), in addition to the known compounds EPI743 and Idebenone, FIG. 4B R-T ($R^4$=H, X=Cl) and R-T ($R^4$=H, X=formate), FIG. 4C R,R—$X^{II}$ ($R^4$=H, X=Cl) and R,R—X ($R^4$=H, X=formate), FIG. 4D R,S—$X^{II}$ ($R^4$=H, X=Cl) and R,S—X ($R^4$=H, X=formate) and FIG. 4E R,trans-$AE^{II}$ ($R^4$=H, X=Cl) and R,trans-AE ($R^4$=H, X=formate).

EXAMPLES

Example 1. Syntheses of the Compounds

Figure 1:
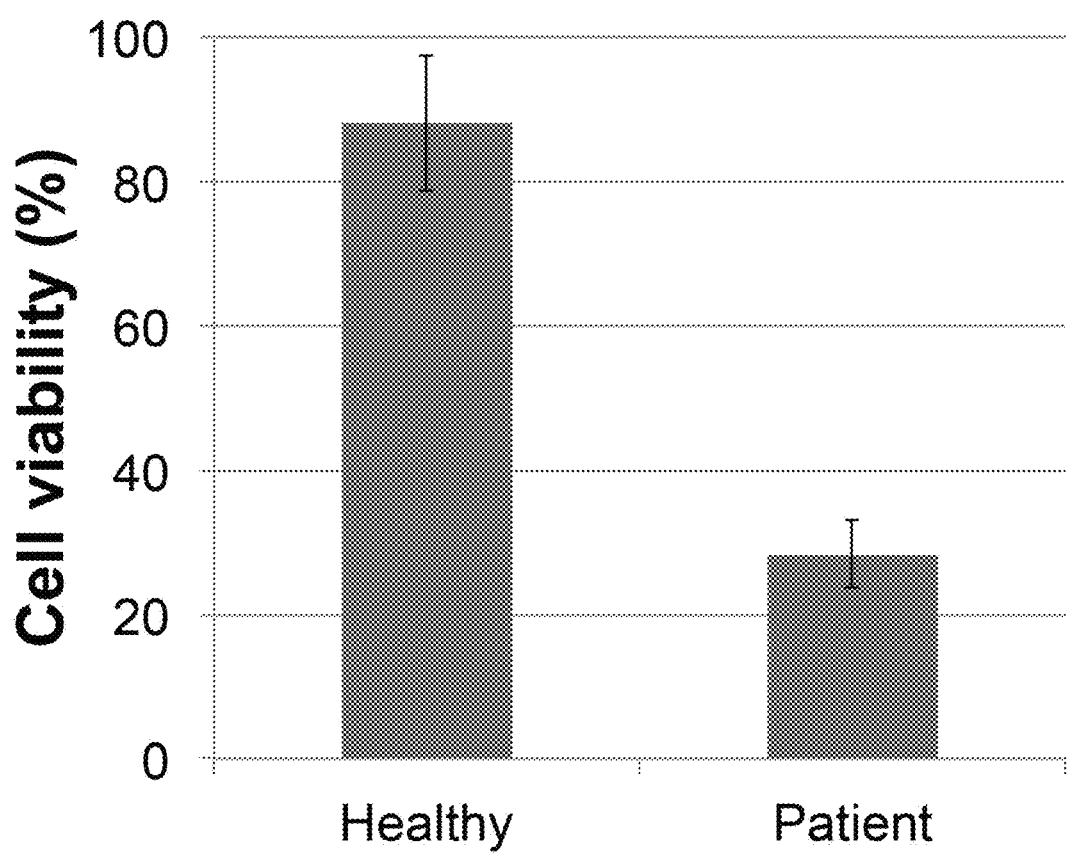
FIG. 1. Effect of L-buthionine-(S,R)-sulfoximine (BSO), an inhibitor of glutathione synthesis, on the viability of primary human fibroblasts derived from healthy individuals or derived from Complex-I deficient patients. Two days after treatment of 48 h with 200 µM BSO, cells were washed and stained with Calcein-AM. Cell viability was determined as a function of fluorescence intensity.

Synthesis of the compounds according to the invention was performed by first preparing the closed chroman derivative of general structure (II). These closed-form derivatives of the compounds according to the invention are designated with an superscript II. For example, the closed form of compound T as defined above is referred to as compound $T^{II}$. Compounds of general structure (II) are prepared according to WO 2014/011047.

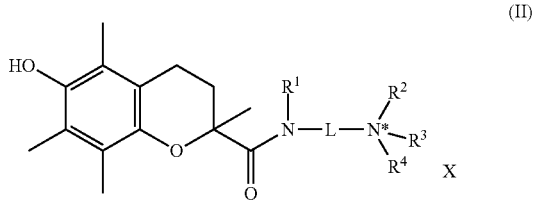

Unless noted otherwise, materials were purchased from commercial suppliers and used as received. $CH_2Cl_2$ (DCM) was freshly distilled from calcium hydride. All air and moisture sensitive reactions were carried out under an inert atmosphere of dry nitrogen. Column chromatography was performed using Acros silica gel (0.035-0.070 mm, 6 nm).

GENERAL PROCEDURE A for the EDCI/HOAt coupling of amines to Trolox™: To a mixture of Trolox™ (1 eq) and amine (1 eq) in DMF (dry, ~0.2M) under nitrogen atmosphere were added EDCI.HCl (1.1 eq) and HOAt (0.1 eq). The mixture was stirred at room temperature until complete conversion (LCMS). The mixture was diluted with $H_2O$ (20 mL) and extracted with EtOAc (3×20 mL). The combined organic phases were successively washed with 0.5M $KHSO_4$ (20 mL), sat. aq. $NaHCO_3$ (20 mL) and brine (3×20 mL). The organic phase was dried over $Na_2SO_4$, filtered and concentrated in vacuo, to obtain intermediate A.

GENERAL PROCEDURE B for BOC-deprotection: To a solution of intermediate A (1 eq) in DCM (~0.03M) was added 4N HCl in dioxane (36 eq). The mixture was stirred at room temperature until complete conversion (LCMS), concentrated, coevaporated with DCM (2×), purified by reversed phase column chromatography ($H_2O$+0.01% (w/w) formic acid/MeCN) and freeze-dried.

GENERAL PROCEDURE C for the ring opening of the chroman derivatives: The compound of formula (II) was oxidized with cerium ammonium nitrate (CAN) or with Iron(III) chloride hexahydrate in the presence of water and acetonitrile as solvent. The compound of formula (II) (0.2 mmol; 1 eq) was dissolved in MeCN (4 ml). Cerium(IV) diammonium nitrate (2.1 eq) was dissolved in $H_2O$ (800 µl) to form an orange solution, and added to the reaction mixture. The mixture was stirred for 30 min at room temperature (colour changed from orange to dark yellow). Then a sample was taken and analysed by LCMS: in all instances complete and clean conversion of starting material into one peak with mass of the desired compound was observed. The reaction mixture was quenched by addition of solid $NaHCO_3$ (3 eq.). The mixture (colour changed from dark yellow to yellow) was stirred for 45 min at room temperature and then the MeCN was removed under reduced pressure. 3 ml $H_2O$ was added and the solids were filtered off and washed with water. The filtrate was partially concentrated and directly purified by reversed phase column chromatography (12 g C18 material, eluens MeCN and $H_2O$+0.01% (w/w) formic acid, collected at 225 nm and 265 nm): (1) 3 min 0% MeCN; (2) 13 min 0% to 100% MeCN; and (3) 3 min 100% MeCN. The pure fractions were combined and freeze-dried overnight to obtain the product in 40-80% yield as a fluffy solid.

All compounds of general structure (II) and of general structure (I) are obtained as formate salts, in other words $R^4$=H, X=formate. These formate salts are used in the examples here below. Thus, even if not indicated, $R^4$=H and X=formate. Compound S,R—X was also prepared as HCl salt, by using 0.01% (w/w) HCl solution during reversed phase column chromatography. In examples 2-4, the HCl salt of compound S,R—X was also tested, and no difference in activity compared to the formate salt of compound S,R—X, of which the results are present below, was observed.

Example 2. Effect of the Compounds on Oxidative Stress-Induced Cell Death

Methods: To assess the ability of the compounds to protect patient cells against oxidative stress-induced cell death an assay was established using stressed primary human fibroblasts derived from a Complex-I deficient patient. Utilizing the inherent oxidative stress of fibroblasts from patients with mitochondrial disease, their oxidative burden was further increased by depleting cellular glutathione with an inhibitor of glutathione synthesis, L-buthionine-(S,R)-sulfoximine (BSO). As a result, while fibroblasts from healthy individuals retained full viability, patient fibroblasts exhibited complete cell death within 48 h of the BSO insult (200 µM) (FIG. 1).

Cells were seeded at a density of 3000 cells/well in a 96-well format plate and incubated with increasing concentrations of compounds in combination with BSO (200 µM, Sigma-Aldrich). Two days after treatment, the cells were washed twice and stained with a solution of 5 µM Calcein-AM (Life technologies C3100MP) during 25 min in 199 medium without phenol red (Life technologies, 11043-023) at 37° C., 5% $CO_2$. After 2 washes with PBS the plate was read on a fluorescence plate reader (Fluostar Omega, BMG labtech) and the percentage of cell viability was determined as a function of fluorescence intensity (FIG. 2).

Results: The tested compounds are shown in the table below. Except for Trolox and open Trolox, all compounds are in salt form, i.e. $R^4$=H and X=formate.

-continued
| Closed compounds | Open compounds |
|---|---|
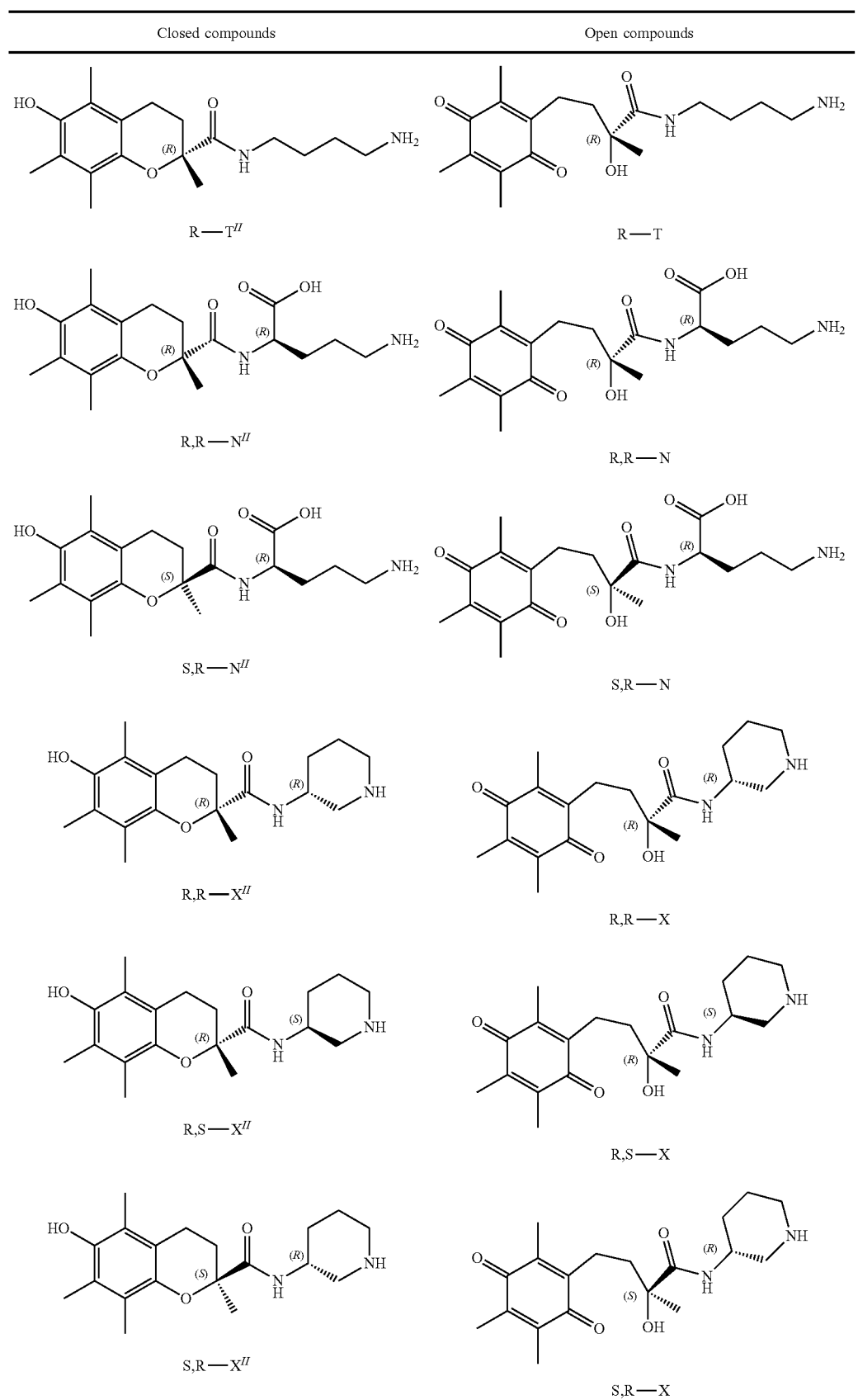

| Closed compounds | Open compounds |
|---|---|
| 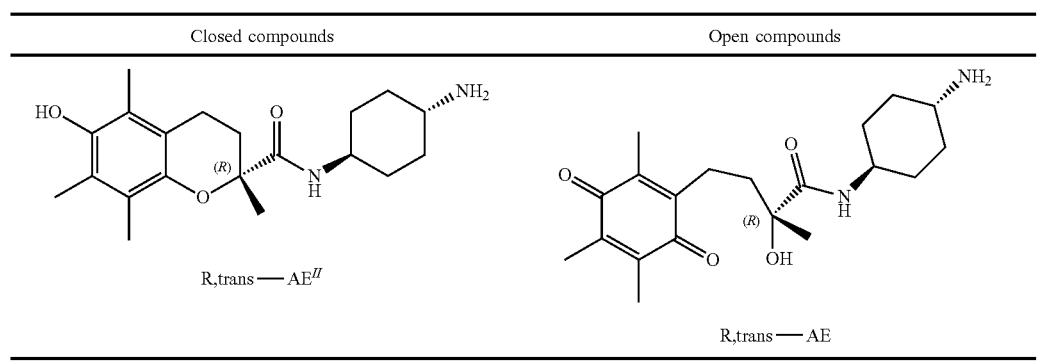 | |
| R,trans—AE$^{II}$ | R,trans—AE |

For each experiment, the closed and corresponding open compound was tested for the ability to protect cells against oxidative stress-induced cell death. As shown in FIG. 2A-2H, the open compound outperformed the corresponding closed compound in each case. Hence, the open compounds are more potent in protecting cells against oxidative stress-induced cell death as compared to the corresponding closed compound.

Figure 2A:
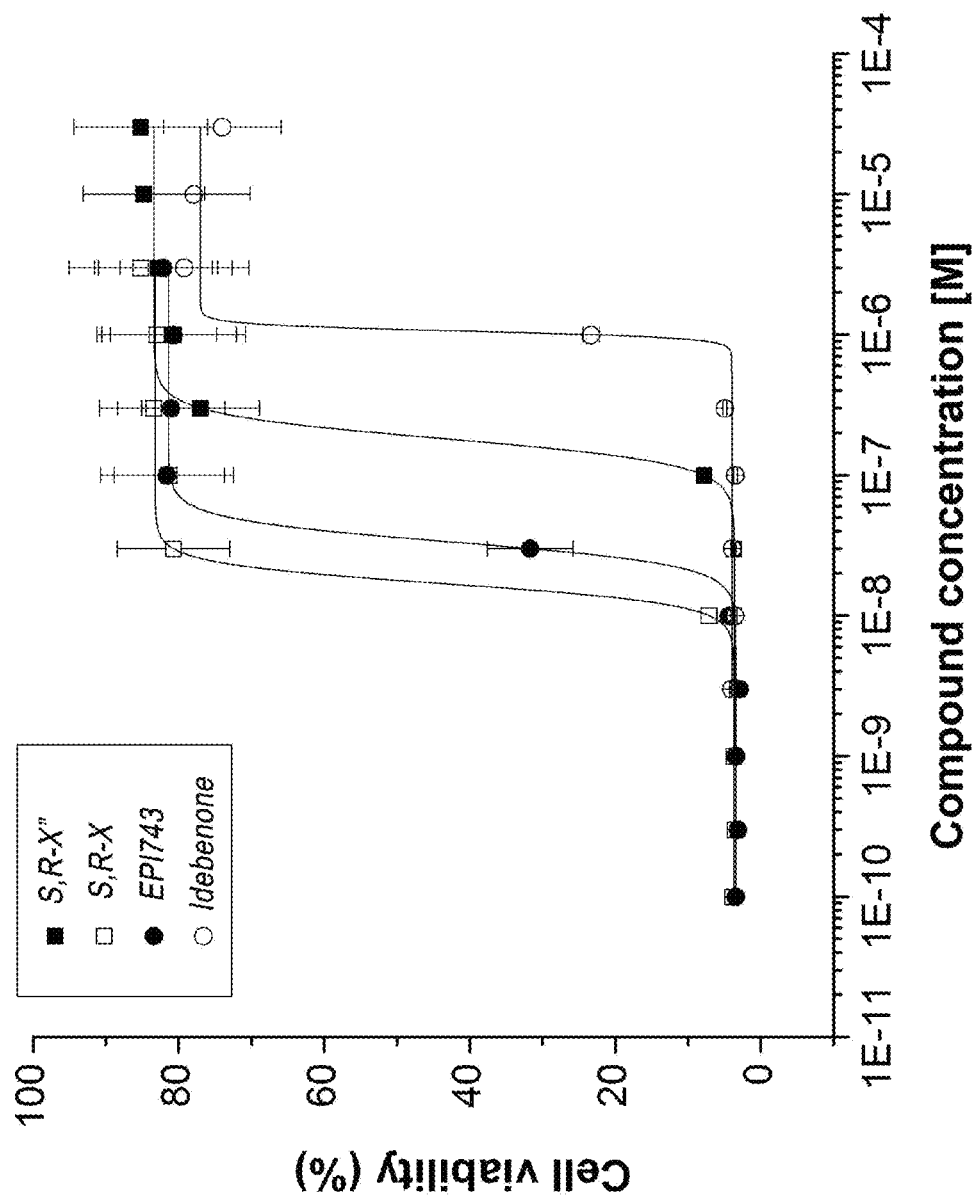
FIG. 2A-FIG. 2H Effect of the compounds on oxidative stress-induced cell death. Primary human fibroblasts derived from Complex-I deficient patients were treated with increasing concentrations of the compounds in combination with 200 µM BSO. After 2 days the cells were washed, stained with Calcein-AM and the fluorescence was measured. Cell viability is depicted as normalized against untreated cells. Each graph depicts the potency of the closed form and corresponding open form of the compound to prevent cell death at selected concentrations.
Figure 2B:
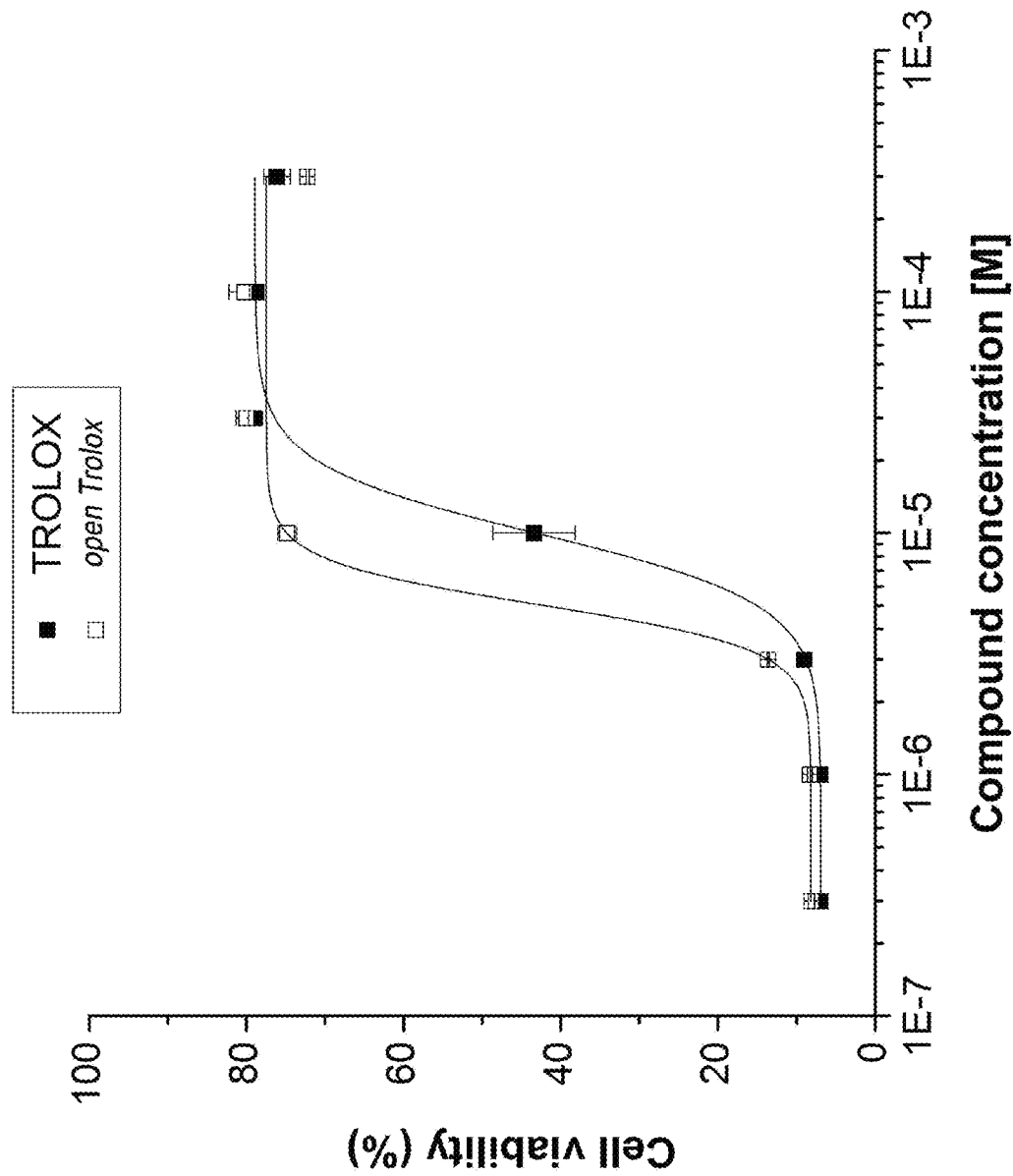
Figure 2C:
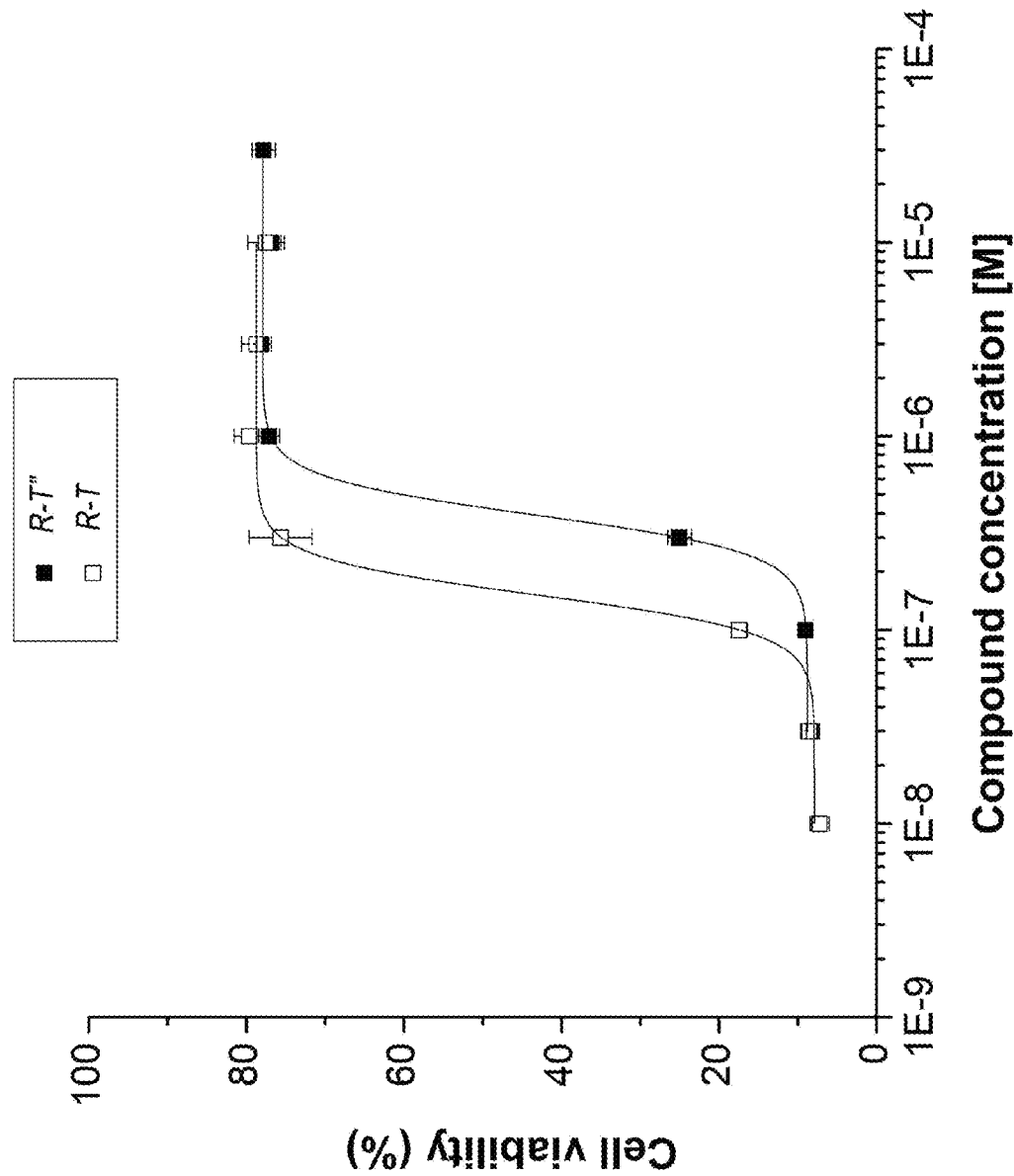
Figure 2D:
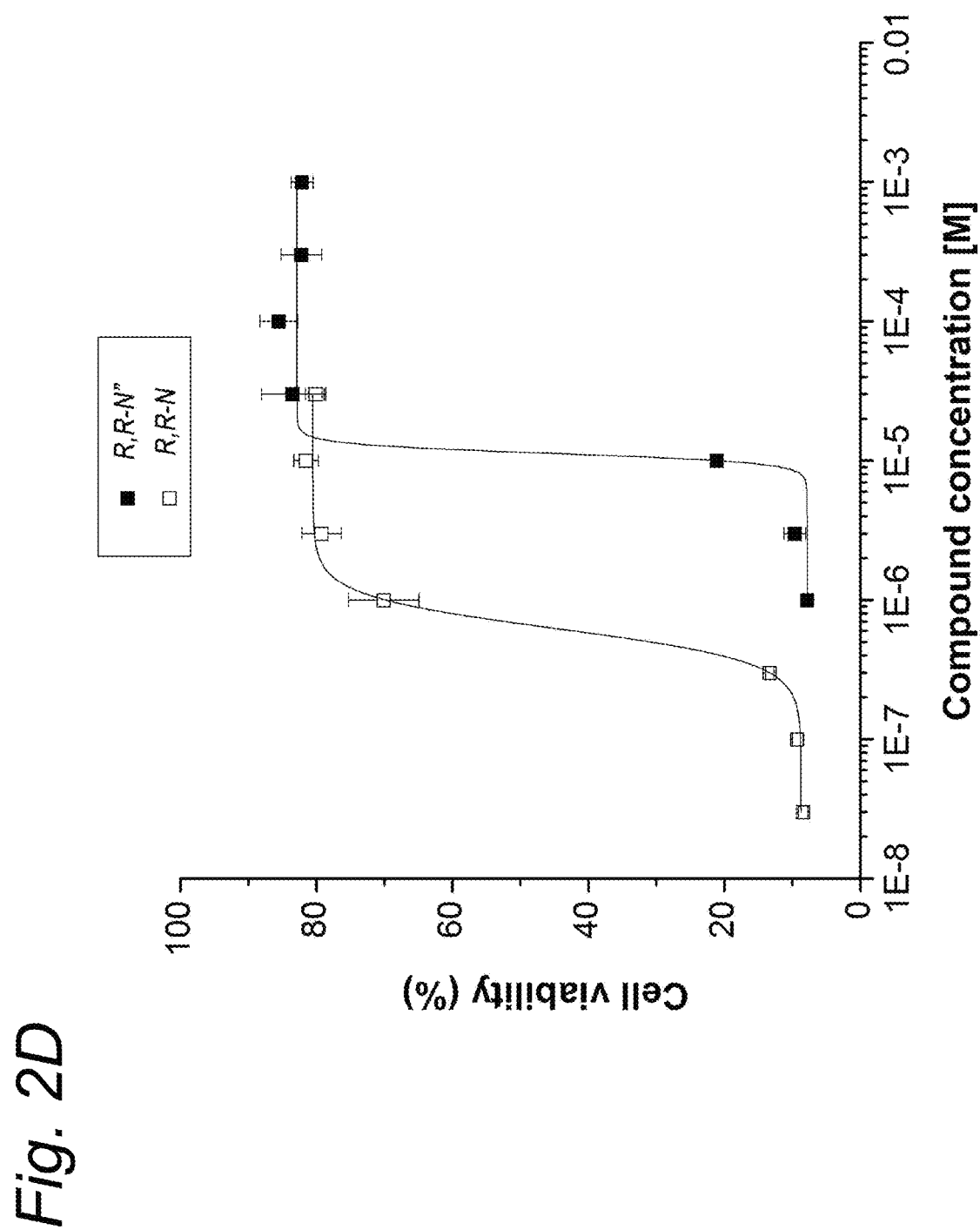
Figure 2E:
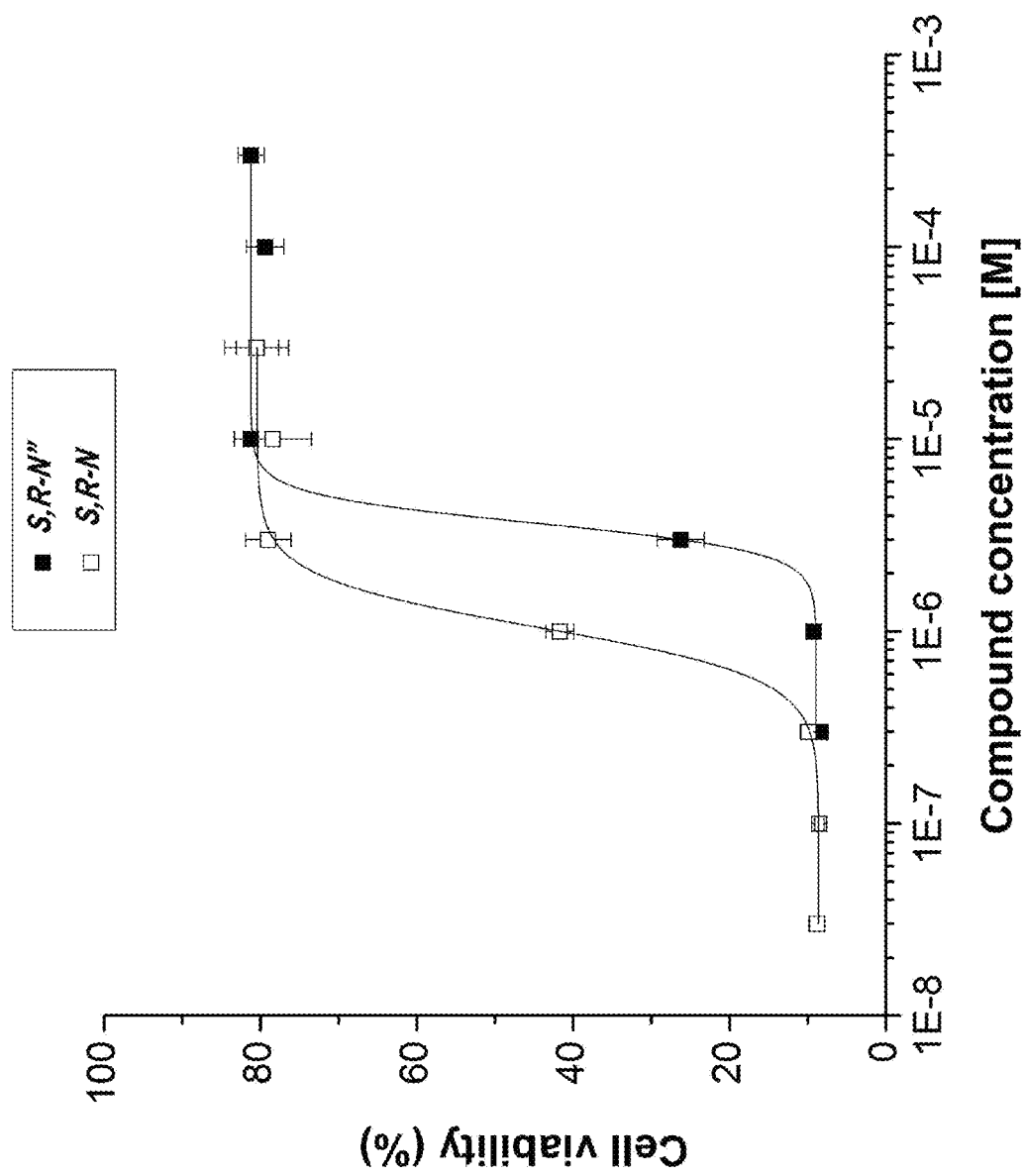
Figure 2F:
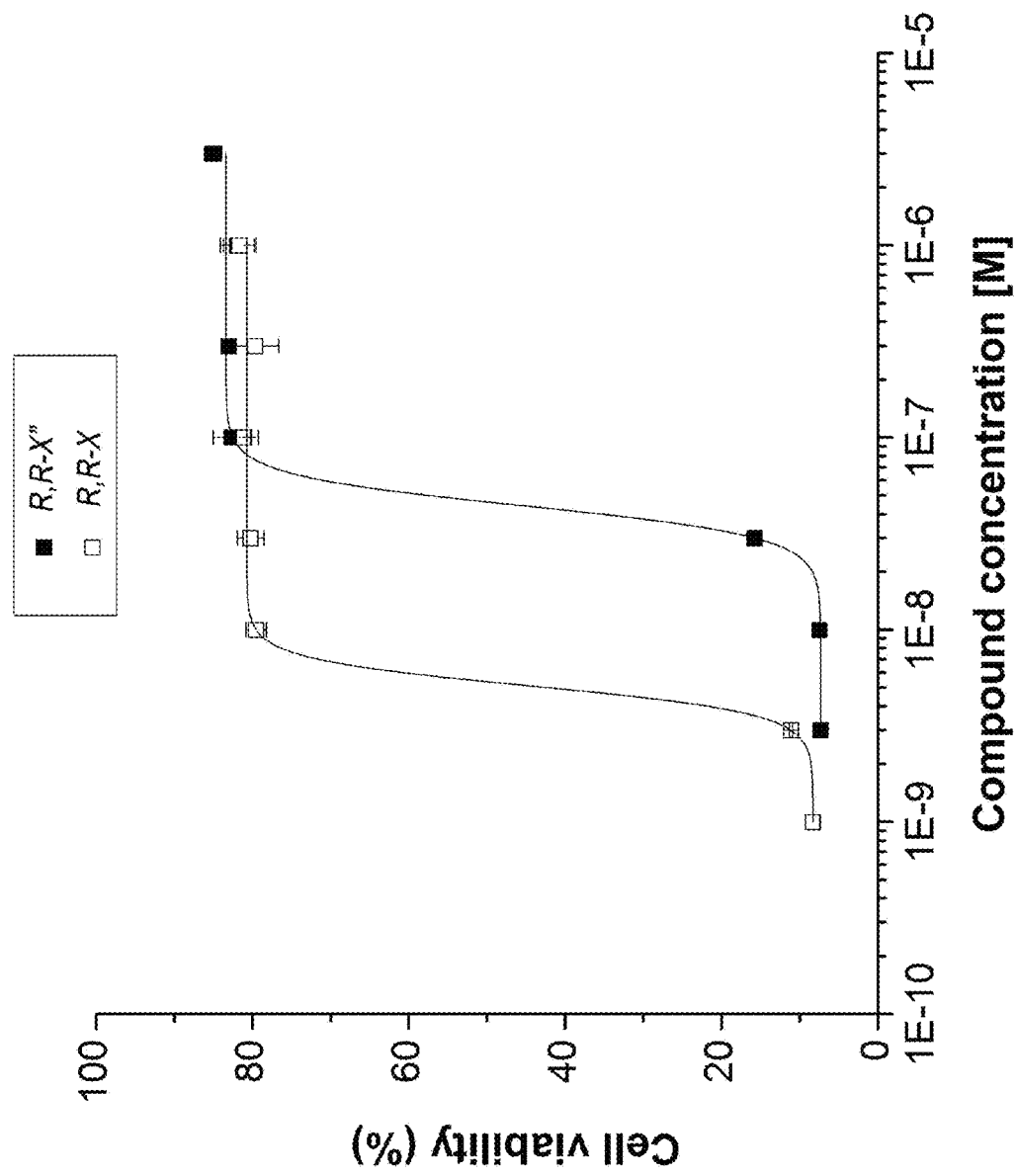
Figure 2G:
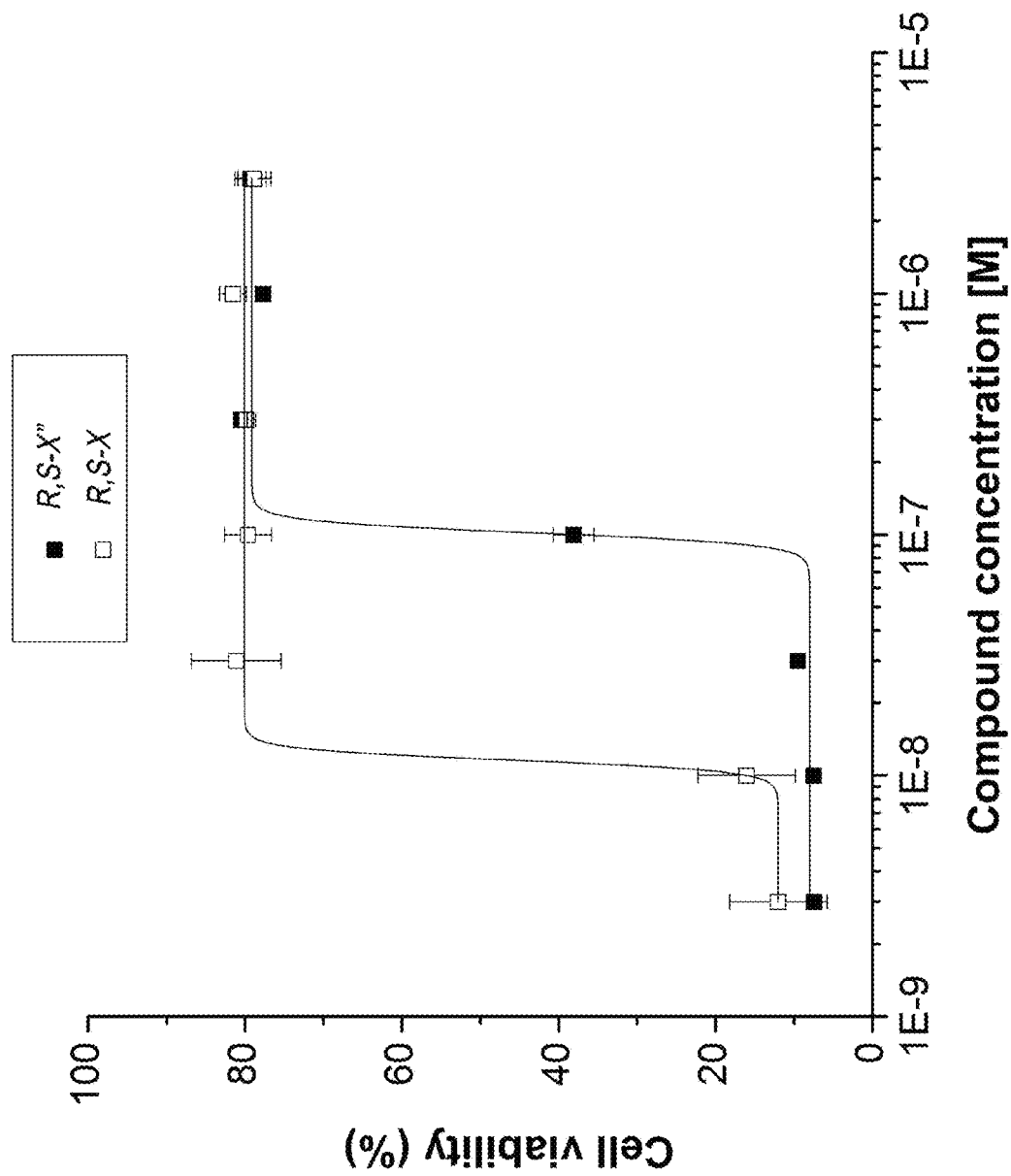
Figure 2H:
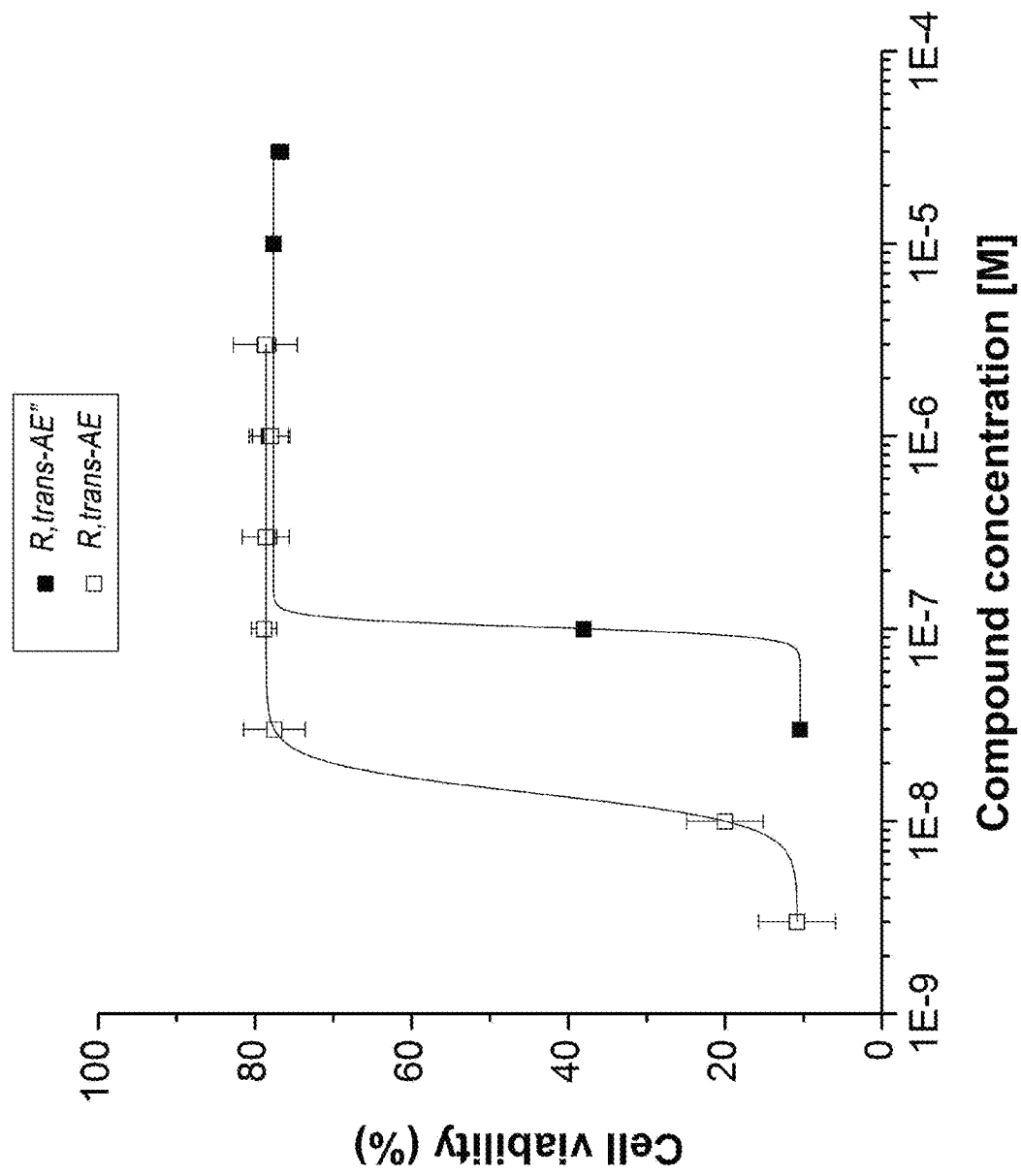

In addition as shown in FIG. 2A, the open-form compound S,R—X is also more potent than the known compounds EPI743 from Edison pharmaceutical and Idebenone from Santhera in protecting the cells against oxidative stress-induced cell death. In particular, the $EC_{50}$ for S,R—X was 16.71 (+/−5.19) nM, while the $EC_{50}$ for EPI743 and Idebenone was respectively 35.32 (+/−4.12) nM and 1469.70 (+/−97.10) nM.

Example 3. Effect of the Compounds on Cellular ROS Levels

Methods: CM-H$_2$DCFDA is a cell-permeable reporter molecule for reactive oxygen species (ROS) that is converted into non-fluorescent and membrane-impermeable CM-H$_2$DCF following removal of its acetate groups by intracellular esterases. Upon oxidation by ROS, CM-H$_2$DCF is converted into fluorescent CM-DCF. It is widely accepted that a wide variety of ROS can be responsible for the CM-H$_2$DCF oxidation, making it a suitable reporter of cellular oxidant levels. The average cellular CM-DCF fluorescence intensity is considered an indirect measure of cellular ROS levels.

The effect of the compounds on the intracellular ROS levels was measured in response to an induction of ROS by hydrogen peroxide. Primary human fibroblasts derived from a patient with mitochondrial disease were seeded at a density of 2500 cells/well in a 96-well format plate. The following day, the culture medium was replaced with 100 μl M199 medium without FBS and phenol red and containing CM-H$_2$DCFDA at a final concentration of 5 μM (Life Technologies). The cell culture plate containing CM-H$_2$DCFDA was placed for 20 minutes at 37° C., 5% CO$_2$. Next, the cells were washed twice with PBS, and 100 μl M199 medium without FBS and phenol red and containing the compounds (final conc. 10 μM) was added to each well. Wells without cells were used to correct for the background fluorescence. The plate was read on a fluorescence plate reader (Fluostar Omega, BMG labtech) in a kinetic mode with a 2 min interval cycle. After 4 cycles, H$_2$O$_2$ (final concentration 100 μM) was added using onboard injectors and the fluorescence measurement was resumed for 1 hour. After background correction the fluorescence intensities were plotted as a function of time.

Figure 3:
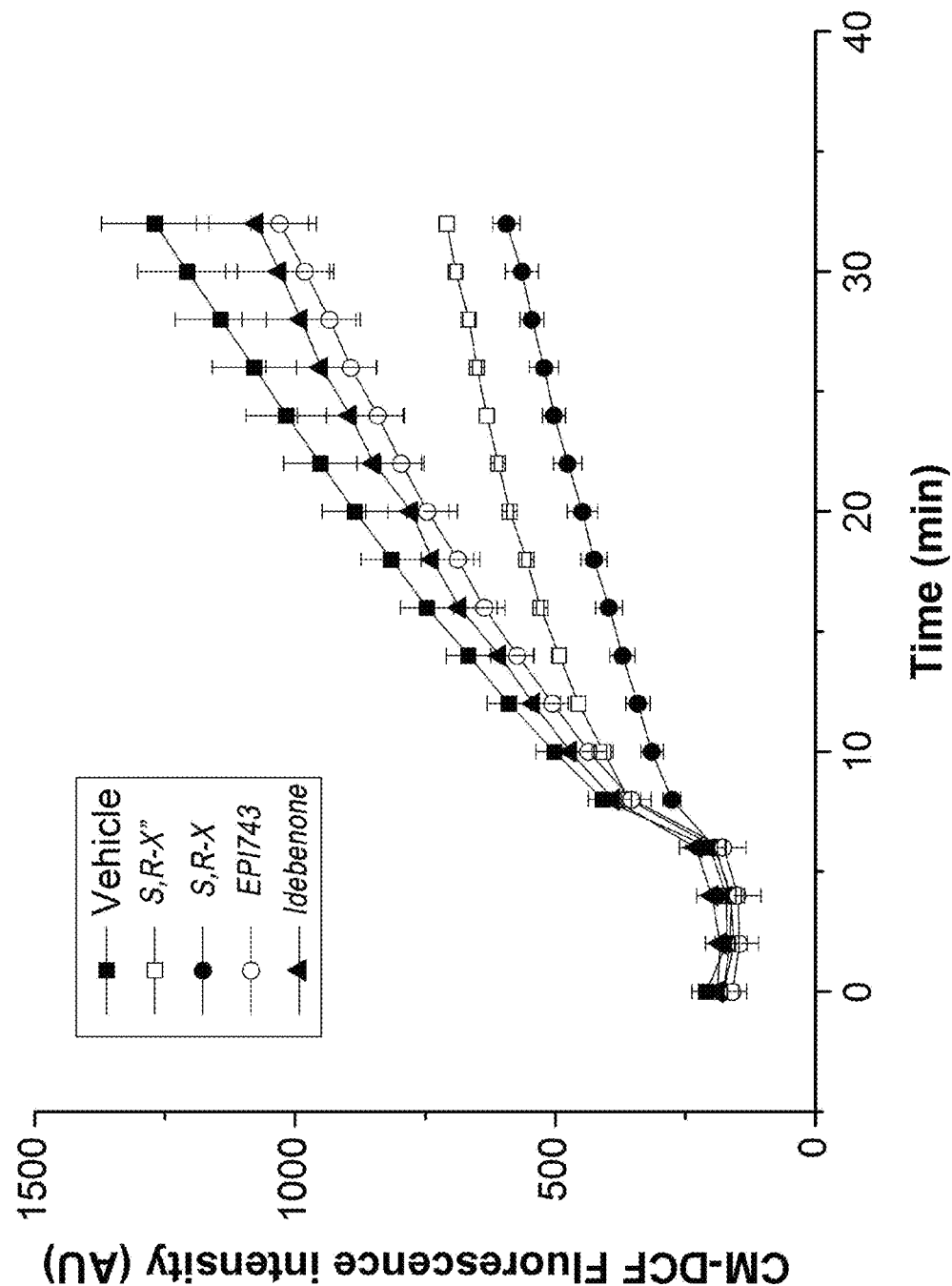
FIG. 3. The effect of the compounds on cellular ROS levels. Primary human fibroblasts derived from Complex-I deficient patients were incubated with 5 µM CM-$H_2$DCFDA for 20 minutes, followed by the addition of the compound EPI743, Idebenone, S,R—$X^{II}$ ($R^4$=H, X=Cl) or S,R—X ($R^4$=H, X=formate), all with a final concentration 10 µM. Untreated cells (vehicle) served as controls. Approximately 8 min. after the addition of the compounds, $H_2O_2$ was added to a final concentration of 100 µM and CM-DCF fluorescence was measured for 30 minutes.

Results: As depicted in FIG. 3, the addition of H$_2$O$_2$ led to a significant increase in cellular CM-DCF fluorescence. CM-DCF fluorescence intensity is a measure of cellular ROS levels, indicating that H$_2$O$_2$ increased intracellular ROS levels. This H$_2$O$_2$-mediated induction of cellular ROS levels was slightly diminished after the addition of the commercially available compound Idebenone from Santhera or after the addition of EPI743 from Edison pharmaceutical. The addition of S,R—X$^{II}$ further damped the H$_2$O$_2$-mediated induction of ROS levels. Strikingly the compound S,R—X, which is the corresponding open form of S,R—X$^{II}$, was significantly more potent than S,R—X$^{II}$ (and EPI743 and Idebenone) in limiting H$_2$O$_2$-mediated induction of ROS levels (FIG. 3).

Example 4. Effect of the Compounds on Intracellular Superoxide Production

Methods: HEt (Hydroethidine) is a non-fluorescent compound, which can enter the cells freely. There it is oxidized by superoxide to its fluorescent products E$^+$ and 2OHE$^+$, which accumulate in negatively charged cellular compartments (i.e. nucleus and mitochondria). E$^+$+2OHE$^+$ fluorescence is thus considered a measure of superoxide production within the cell.

The effect of the compounds on the intracellular superoxide levels was measured. Primary human fibroblasts obtained from a patient with mitochondrial disease were seeded at a density of 3000 cells/well in a 96-well format. The following day, the culture medium was replaced with 100 μl medium containing the compounds at different concentrations. After approximately 24 hours the cells were incubated with 100 μL medium without FBS and phenol red and containing HEt at a final concentration 10 μM (Life Technologies). The cell culture plate containing HEt was placed for 10 minutes at 37° C., 5% CO$_2$. Next, the cells were washed twice with medium, placed in culture medium without FBS and phenol red and visualized by fluorescence microscopy (BD Pathway 855, BDBiosciences). From the obtained images superoxide levels were analysed using using Image Pro plus (Media Cybernetics) software.

Figure 4A:
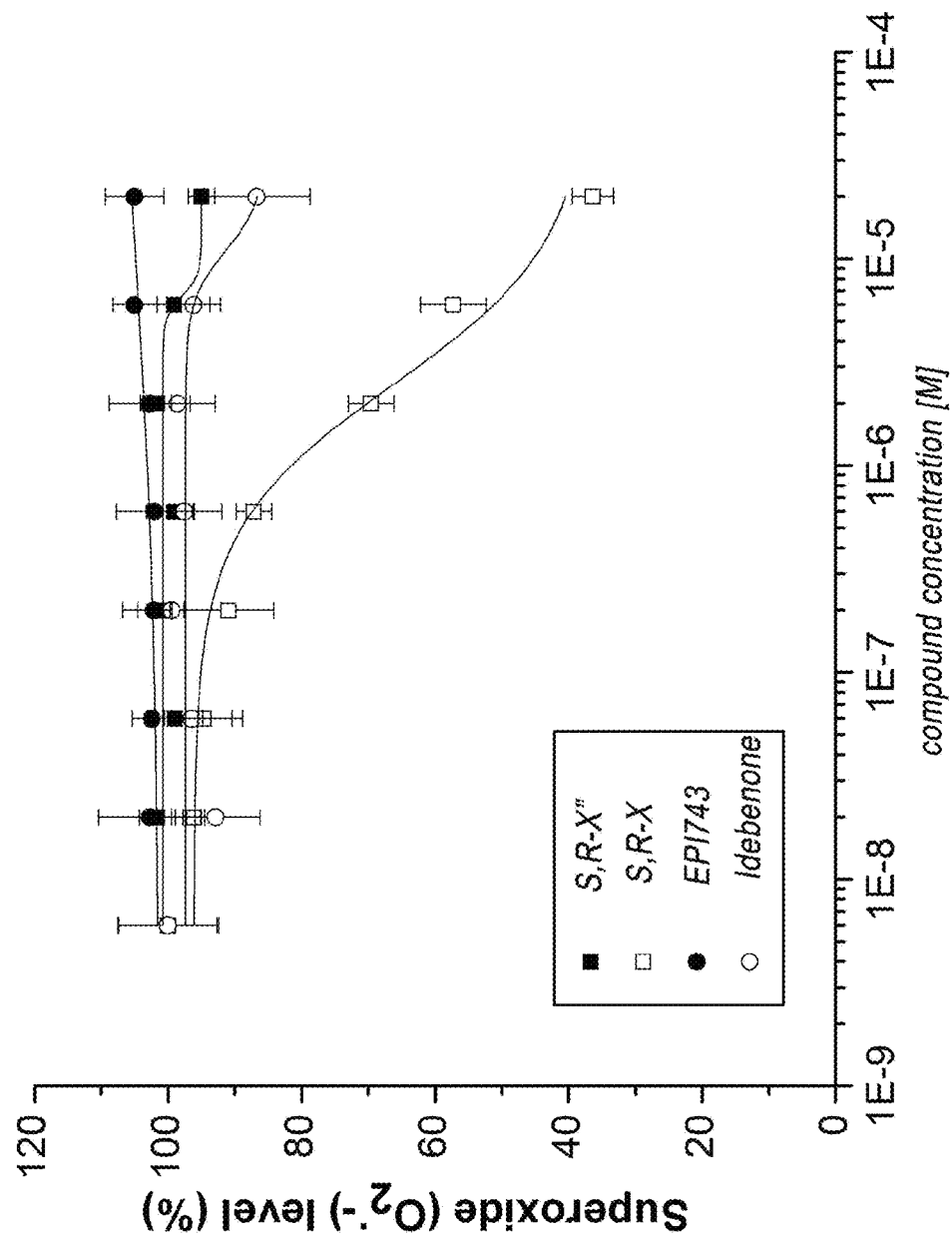
FIG. 4A-FIG. 4E Effect of the compounds on cellular superoxide production. Primary human fibroblasts derived from Complex-I patients were incubated with increasing concentrations of the compounds. The following days cells were stained with Hydroethidine (Het) (10 µM) and fluorescence was measured. Results are depicted as percentage of vehicle-treated cells.
Figure 4B:
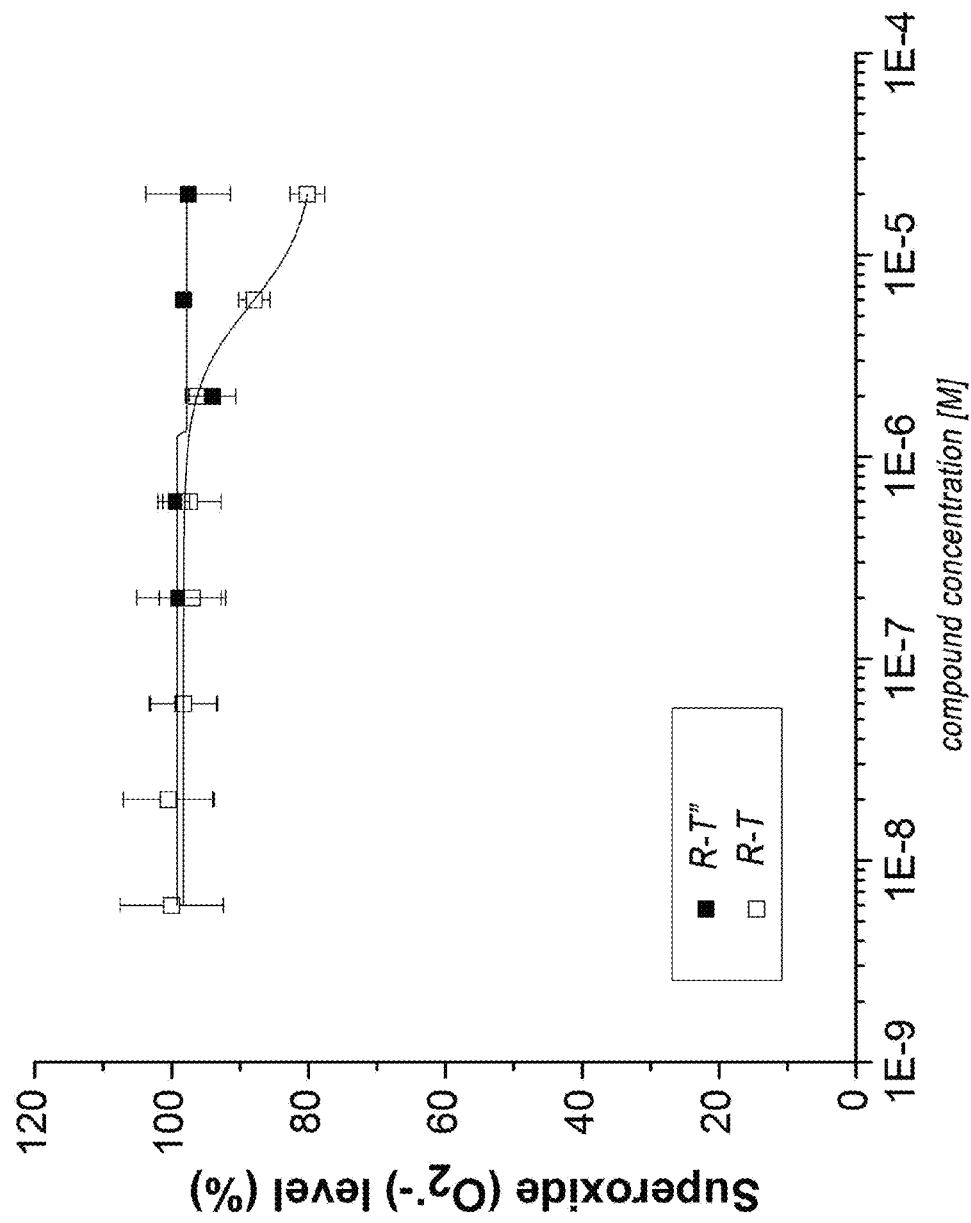
Figure 4C:
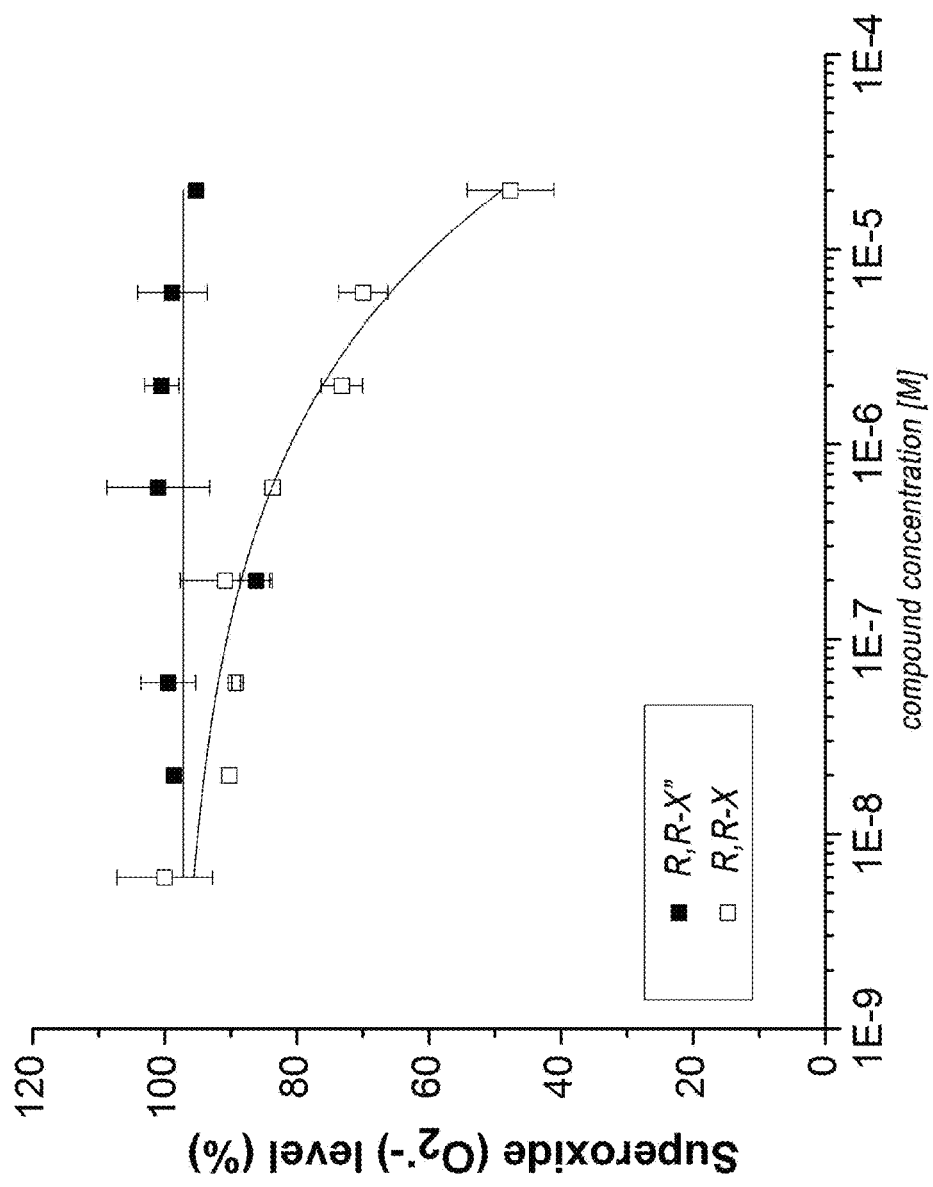
Figure 4D:
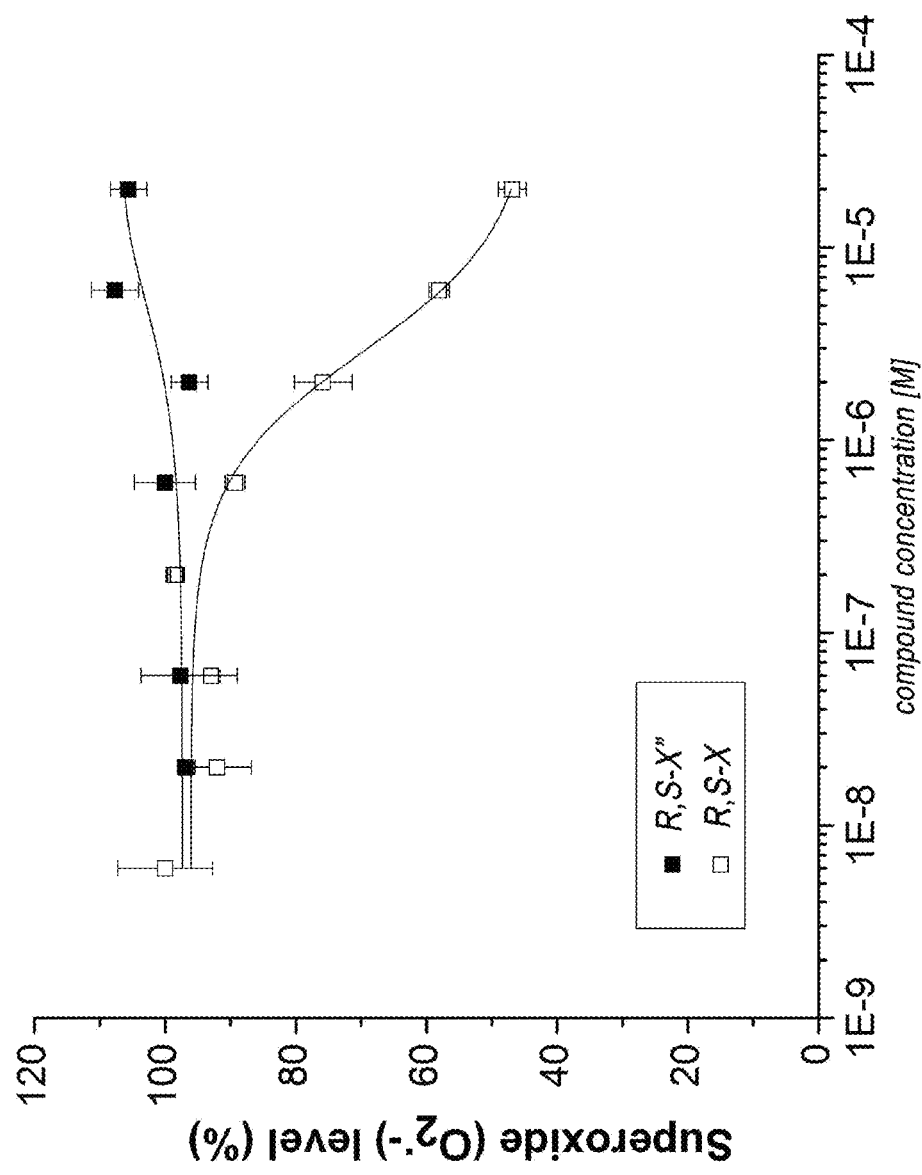
Figure 4E:
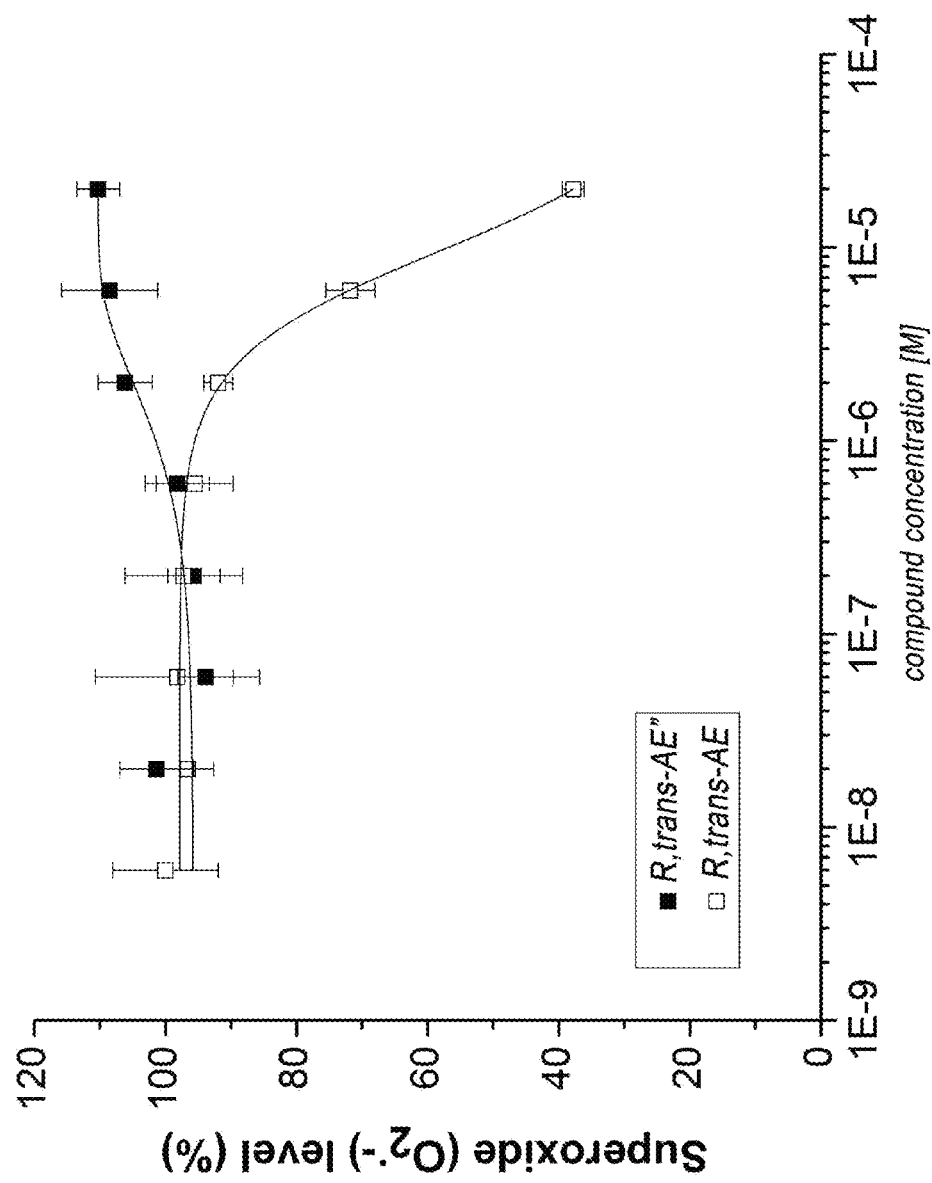

Results: Selected compounds were tested for their superoxide scavenging capabilities. As indicated in FIG. 4A, the compounds S,R—X$^{II}$, EPI743 (Edison pharmaceutical) and Idebenone (Santhera) demonstrated only a limited ability to scavenge superoxide. In contrast the compound S,R—X, which is the corresponding open-form of S,R—X$^{II}$, significantly lowered superoxide levels (FIG. 4A). In fact as indicated in FIG. 4A-E, each of the tested open-form compounds was more potent than the corresponding closed-form compound in scavenging superoxide, especially at higher concentrations. Hence, the open-form compounds are more potent than their closed counterparts in scavenging intracellular superoxide.

The invention claimed is:

1. A compound of general structure (I):

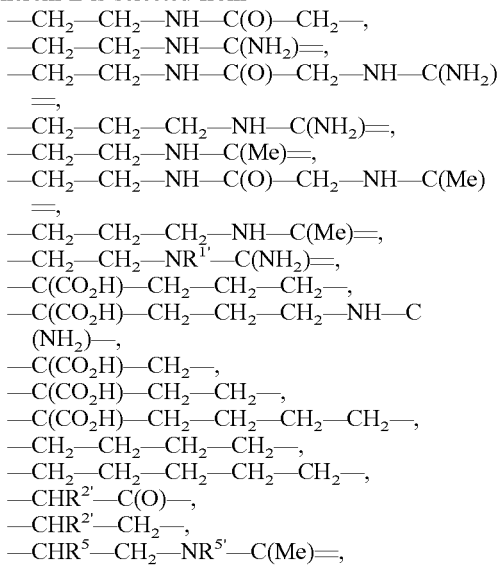

wherein
wherein L is selected from
—$CH_2$—$CH_2$—NH—C(O)—$CH_2$—,
—$CH_2$—$CH_2$—NH—C($NH_2$)=,
—$CH_2$—$CH_2$—NH—C(O)—$CH_2$—NH—C($NH_2$) =,
—$CH_2$—$CH_2$—$CH_2$—NH—C($NH_2$)=,
—$CH_2$—$CH_2$—NH—C(Me)=,
—$CH_2$—$CH_2$—NH—C(O)—$CH_2$—NH—C(Me) =,
—$CH_2$—$CH_2$—$CH_2$—NH—C(Me)=,
—$CH_2$—$CH_2$—$NR^{1'}$—C($NH_2$)=,
—C($CO_2H$)—$CH_2$—$CH_2$—$CH_2$—,
—C($CO_2H$)—$CH_2$—$CH_2$—$CH_2$—NH—C($NH_2$)—,
—C($CO_2H$)—$CH_2$—,
—C($CO_2H$)—$CH_2$—$CH_2$—,
—C($CO_2H$)—$CH_2$—$CH_2$—$CH_2$—$CH_2$—,
—$CH_2$—$CH_2$—$CH_2$—$CH_2$—,
—$CH_2$—$CH_2$—$CH_2$—$CH_2$—$CH_2$—,
—$CHR^{2'}$—C(O)—,
—$CHR^{2'}$—$CH_2$—,
—$CHR^5$—$CH_2$—$NR^{5'}$—C(Me)=,
—$CHR^{2'}$—$CH_2$—$CH_2$—,
—$CH_2$—$CH_2$—$CHR^{1'}$—,
—$CH_2$—$CH_2$—$CHR^{1'}$—NH—C(O)—C(Me)-,
—$CH_2$—$CHR^{1'}$—,
—$CH_2$—$CHR^{1'}$—NH—C(Me)=, or
—$CHR^5$—$CH_2$—$CH_2$—$CHR^{5'}$—;

$R^1$ and $R^2$ are each independently selected from H, $C_1$-$C_6$ alkyl or $C_1$-$C_6$ alkenyl, or $R^1$ is joined with $R^{1'}$ in a cyclic structure and/or $R^2$ is joined with $R^{2'}$ in a cyclic structure, or $R^1$ and $R^2$ are joined together and thus form a second linker between the amide nitrogen atom and the distal nitrogen atom (N*) wherein L is a linker comprising 1 to 10 optionally substituted backbone atoms selected from carbon, nitrogen and oxygen;

$R^3$ is selected from H, $C_1$-$C_6$ alkyl or $C_1$-$C_6$ alkenyl, wherein the alkyl or alkenyl moiety may be substituted with one or more halogen atoms or (halo) alkoxy moieties, or $R^3$ is absent when the distal nitrogen atom is part of an imine moiety; and $R^4$ is absent; and $R^5$ is joined with $R^{5'}$ in a cyclic structure, and X is absent.

2. The compound according to claim 1, wherein $R^2$ is joined with a backbone atom of the linker L in a saturated cyclic structure.

3. The compound according to claim 2, wherein $R^2$ is joined with a backbone atom of the linker L in a piperidine ring.

4. The compound according to claim 1, wherein
L=—C($CO_2H$)($CH_2$)$_3$—, $R^1$=$R^2$=$R^3$=H;
L=—($CH_2$)$_4$—, $R^1$=H, $R^2$=$R^3$=Me;
L=—$CHR^{2'}CH_2$— $R^1$=$R^3$=H, $R^2$-$R^{2'}$=—($CH_2$)$_3$—;
L=—$CHR^5$($CH_2$)$_2CHR^{5'}$—, $R^1$=$R^2$=$R^3$=H, $R^5$-$R^{5'}$=—($CH_2$)$_2$—; or
L=—$CHR^5$($CH_2$)$_2CHR^{5'}$—, $R^1$=$R^2$=$R^3$=H, and $R^5$-$R^{5'}$=—($CH_2$)$_2$—, which is in the S,R-configuration.

5. A pharmaceutical or cosmetic composition comprising a compound according to claim 1 and a physiologically acceptable carrier.

* * * * *